(12) United States Patent
Naito

(10) Patent No.: US 10,235,766 B2
(45) Date of Patent: *Mar. 19, 2019

(54) RADIOGRAPHIC IMAGE ANALYSIS DEVICE AND METHOD, AND STORAGE MEDIUM HAVING STORED THEREIN PROGRAM

(71) Applicant: FUJIFILM Corporation, Tokyo (JP)

(72) Inventor: Satoshi Naito, Kanagawa-ken (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/857,171

(22) Filed: Dec. 28, 2017

(65) Prior Publication Data

US 2018/0122094 A1   May 3, 2018

Related U.S. Application Data

(63) Continuation of application No. 15/007,724, filed on Jan. 27, 2016, now Pat. No. 9,886,765, which is a
(Continued)

(30) Foreign Application Priority Data

Jul. 31, 2013 (JP) .................................. 2013-159528
Nov. 6, 2013 (JP) .................................. 2013-229941

(51) Int. Cl.
*G06F 9/00* (2006.01)
*G06T 7/60* (2017.01)
(Continued)

(52) U.S. Cl.
CPC .............. *G06T 7/60* (2013.01); *A61B 6/4291* (2013.01); *A61B 6/5211* (2013.01);
(Continued)

(58) Field of Classification Search
CPC ..... A61B 6/5282; A61B 6/461; A61B 6/4291; A61B 6/5211; A61B 6/5294; G06T 2207/10116

See application file for complete search history.

(56) References Cited

U.S. PATENT DOCUMENTS

2004/0096035 A1   5/2004 Yamazaki et al.
2004/0125921 A1   7/2004 Allouche et al.
(Continued)

FOREIGN PATENT DOCUMENTS

JP    62-192640 A    8/1987
JP    2-244881 A    9/1990
(Continued)

OTHER PUBLICATIONS

Communication dated Aug. 2, 2016 from the Japanese Patent Office in counterpart Japanese Application No. 2013-229941.
(Continued)

*Primary Examiner* — Li Liu
(74) *Attorney, Agent, or Firm* — Sughrue Mion, PLLC

(57) ABSTRACT

A subject image is acquired. A virtual model of the subject having a predetermined body thickness distribution is acquired. A composite image of an estimated primary X-ray image, which is obtained by estimating a primary X-ray image of the virtual model obtained by radiography from the virtual model, and an estimated scattered X-ray image, which is obtained by estimating a scattered X-ray image of the virtual model obtained by radiography from the virtual model, is generated as an estimated image which is obtained by estimating a radiographic image of the subject obtained by radiography. The body thickness distribution of the virtual model is corrected such that a difference between the estimated image and the subject image is reduced. The
(Continued)

corrected body thickness distribution of the virtual model is determined as the body thickness distribution of the subject.

20 Claims, 8 Drawing Sheets

Related U.S. Application Data continuation of application No. PCT/JP2014/003802, filed on Jul. 17, 2014.

(51) Int. Cl.
    *A61B 6/00*     (2006.01)
    *G06T 7/62*     (2017.01)
    *G06T 7/00*     (2017.01)

(52) U.S. Cl.
    CPC .......... *A61B 6/5282* (2013.01); *A61B 6/5294* (2013.01); *G06T 7/0012* (2013.01); *G06T 7/62* (2017.01); *G06T 2207/10116* (2013.01)

(56) References Cited

U.S. PATENT DOCUMENTS

| | | | |
|---|---|---|---|
| 2010/0046822 A1* | 2/2010 | Li | A61B 6/00 382/132 |
| 2013/0089176 A1 | 4/2013 | Nabatame | |
| 2015/0063526 A1 | 3/2015 | Kobayashi et al. | |
| 2015/0100290 A1 | 4/2015 | Falt et al. | |

FOREIGN PATENT DOCUMENTS

| | | |
|---|---|---|
| JP | 10-057361 A | 3/1998 |
| JP | 2003-310592 A | 11/2003 |
| JP | 2004-166724 A | 6/2004 |
| JP | 2008-000190 A | 1/2008 |
| JP | 2008-011894 A | 1/2008 |
| JP | 2010-005032 A | 1/2010 |
| JP | 2011-135990 A | 7/2011 |
| JP | 2012-020009 A | 2/2012 |
| WO | 2009/142166 A1 | 11/2009 |

OTHER PUBLICATIONS

Dinko E. Gonzalez Trotter, et al., "Thickness-dependent Scatter Correction Algorithm for Digital Mammography", Medical Imaging 2002: Physics of Medical Imaging, Proceedings of SPIE, 2002, pp. 469-478, vol. 4682.

H. Kato, "A New Method for Eliminating Scatter Components from a Digital X-ray Image by Later Processing", Japanese Journal of Radiological Technology, Sep. 2006, pp. 1359-1368; Vo. 62, No. 9.

International Search Report for PCT/JP2014/003802 dated Oct. 7, 2014 [PCT/ISA/210].

Written Opinion for PCT/JP2014/003802 dated Oct. 7, 2014 [PCT/ISA/210].

\* cited by examiner

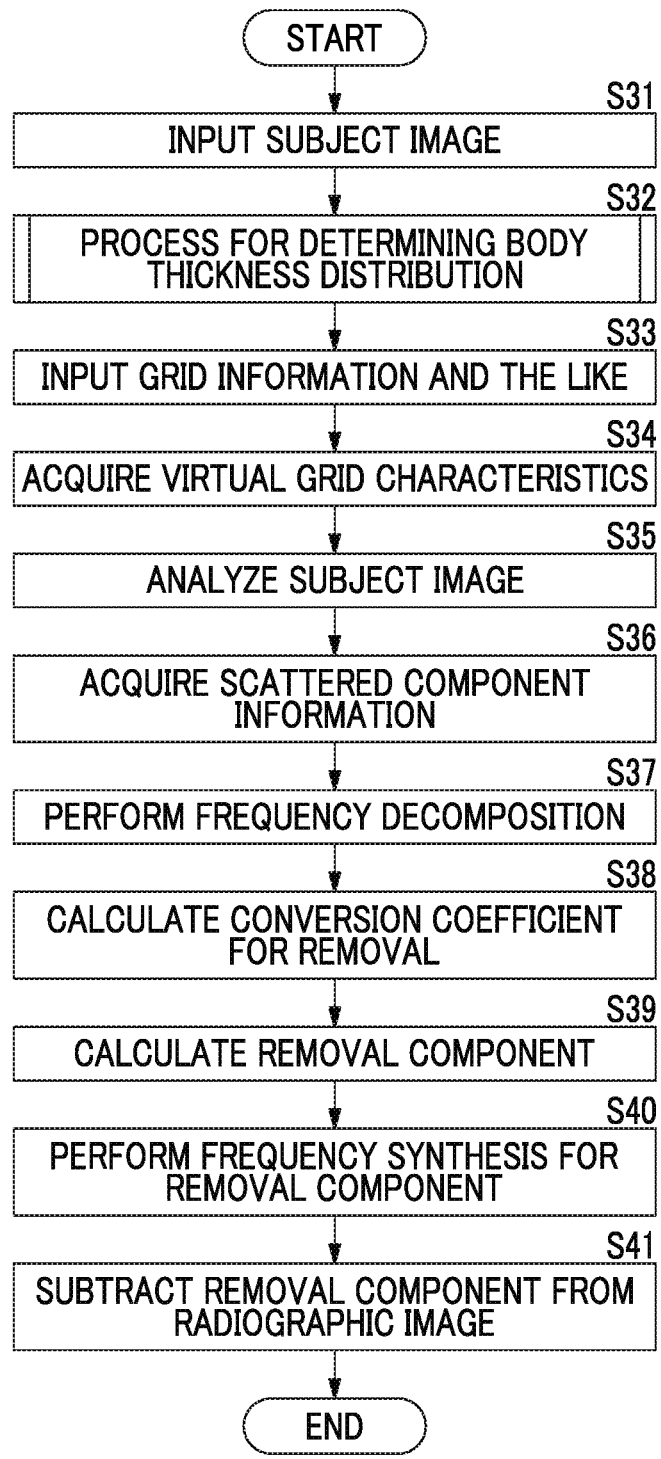

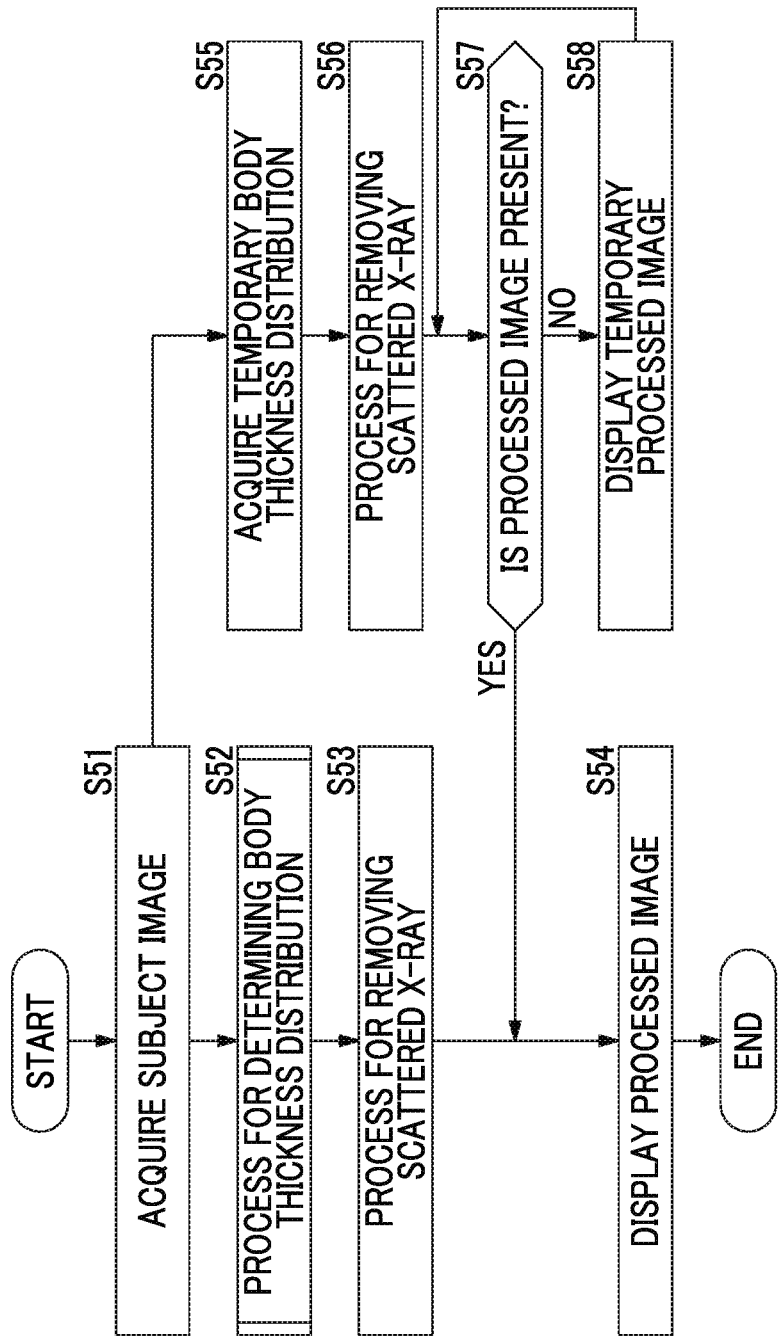

RADIOGRAPHIC IMAGE ANALYSIS DEVICE AND METHOD, AND STORAGE MEDIUM HAVING STORED THEREIN PROGRAM

CROSS-REFERENCE TO RELATED APPLICATIONS

This application is a Continuation of U.S. application Ser. No. 15/007,724 filed Jan. 27, 2016, which is a Continuation of PCT International Application No. PCT/JP2014/003802 filed on Jul. 17, 2014, which claims priority under 35 U.S.C. § 119(a) to Japanese Patent Application No. 2013-159528 filed on Jul. 31, 2013 and Japanese Patent Application No. 2013-229941 filed on Nov. 6, 2013. Each of the above applications is hereby expressly incorporated by reference, in its entirety, into the present application.

BACKGROUND OF THE INVENTION

1. Field of the Invention

The present invention relates to an image analysis device and method and a storage medium having stored therein a program which analyze a radiographic image of a subject obtained by radiography, and more particularly, to an image analysis device and method and a program which analyze a radiographic image of a subject obtained by radiography to estimate the thickness of the subject at each position of the radiographic image.

2. Description of the Related Art

It is known that, when a radiographic image of the subject is captured with radiation passing through the subject, the influence of the scattering of radiation or a reduction in the transmissivity of radiation in the subject increases as the thickness of the subject increases, which results in a change in the quality of the acquired radiographic image. Therefore, a technique has been proposed which roughly estimates the thickness of the subject, on the basis of various kinds of information, such as imaging conditions, a signal value of a radiographic image, the histogram width of the signal value of the radiographic image, and the length of the subject in the subject image in a predetermined direction and changes the conditions of image processing, such as a process of removing scattered X-rays of the captured radiographic image, or imaging conditions applied to the capture of the radiographic image, on the basis of the estimated thickness of the subject.

For example, JP1990-244881A (JP-H02-244881A) discloses a method which measures the pixel value of an image of a simulated subject with a known thickness, which is captured by radiography under known imaging conditions, prepares an association table in which the body thickness is associated with the pixel value in advance, estimates a rough body thickness distribution according to the pixel value of the subject image, on the basis of the association table, estimates a scattered X-ray component of the subject image corresponding to the body thickness distribution of the subject image, and subtracts the scattered X-ray component from the subject image to acquire a processed image.

Trotter et al., "Thickness-dependent Scatter Correction Algorithm for Digital Mammography", Proc. SPIE Vol. 4682, May 2002, pp. 469-478 discloses a method which estimates a scattered X-ray component of a radiographic image on the basis of a thickness distribution of the human body and removes the scattered X-ray component. According to the image processing method disclosed in Trotter and four others, "Thickness-dependent Scatter Correction Algorithm for Digital Mammography", Proc. SPIE Vol. 4682, May 2002, pp. 469-478, an estimated scattered X-ray image obtained by applying a predetermined function to an input subject image and estimating an image of a scattered X-ray included in the subject image is generated on the basis of the body thickness distribution estimated from the pixel value of the subject image and the estimated scattered X-ray image is subtracted from the subject image to generate an estimated primary X-ray image obtained by estimating a primary X-ray image from the input subject image. In addition, a process of applying a predetermined function to the generated estimated primary X-ray image to generate an estimated scattered X-ray image and subtracting the estimated scattered X-ray image from the subject image to generate an estimated primary X-ray image is repeated until the estimated scattered X-ray image is converged under predetermined convergence conditions, the converged estimated scattered X-ray image is calculated, and the estimated scattered X-ray image is subtracted from the subject image to finally acquire a processed image from which the scattered X-ray component has been removed. In addition, Trotter and four others, "Thickness-dependent Scatter Correction Algorithm for Digital Mammography", Proc. SPIE Vol. 4682, May 2002, pp. 469-478 discloses a method which adjusts a predetermined function for estimating the image of the scattered X-ray included in the subject image on the basis of the body thickness.

SUMMARY OF THE INVENTION

Here, in order to calculate a detailed body thickness in which the internal structure of the subject, such as the lung field in the subject, is reflected, it is preferable to calculate the thickness of the subject from the pixel value of the subject image of the subject which is actually captured. However, the subject image includes a component of the primary X-ray (primary X-ray component) which passes through the subject and is directly emitted to the radiation detector and a component of the scattered X-ray (scattered X-ray component) which is generated by the scattering of radiation in the subject.

Therefore, when the method for estimating the body thickness on the basis of the pixel value is applied to the radiographic image which is captured without using a scattered X-ray removal grid (grid) as in JP1990-244881A (JP-H02-244881A) or Trotter and four others, "Thickness-dependent Scatter Correction Algorithm for Digital Mammography", Proc. SPIE Vol. 4682, May 2002, pp. 469-478, it is difficult to accurately estimate the body thickness distribution of the subject due to the influence of the scattered X-ray component in the radiographic image. In addition, it is considered that the subject image is captured using a grid in order to avoid the influence of the scattered X-ray component. However, there is a demand for accurately estimating the body thickness distribution from the subject image which is captured without using a grid, in order to reduce a burden such as the radiation dose received by the subject.

The invention has been made in view of the above-mentioned problems and an object of the invention is to perform an image analysis process which analyzes a radiographic image captured by irradiating a subject with radiation to accurately estimate a body thickness distribution of the subject.

According to an aspect of the invention, there is provided a radiographic image analysis device that analyzes a subject image of a subject obtained by radiography to estimate a body thickness distribution of the subject. The radiographic image analysis device includes: an image acquisition unit that acquires the subject image; a virtual model acquisition unit that acquires a virtual model of the subject having a predetermined body thickness distribution; an estimated image generation unit that generates a composite image of an estimated primary X-ray image, which is obtained by estimating a primary X-ray image of the virtual model obtained by radiography from the virtual model, and an estimated scattered X-ray image, which is obtained by estimating a scattered X-ray image of the virtual model obtained by radiography from the virtual model, as an estimated image which is obtained by estimating a radiographic image of the subject obtained by radiography; a correction unit that corrects the body thickness distribution of the virtual model such that a difference between the estimated image and the subject image is reduced; and a body thickness distribution determination unit that determines the corrected body thickness distribution of the virtual model as the body thickness distribution of the subject.

According to another aspect of the invention, there is provided a radiographic image analysis method that is performed in a radiographic image analysis device and analyzes a subject image which is obtained by irradiating a subject with radiation to estimate a body thickness distribution of the subject. The radiographic image analysis method includes: an image acquisition step of acquiring the subject image; a virtual model acquisition step of acquiring a virtual model of the subject having a predetermined body thickness distribution; an estimated image generation step of generating a composite image of an estimated primary X-ray image, which is obtained by estimating a primary X-ray image of the virtual model obtained by radiography from the virtual model, and an estimated scattered X-ray image, which is obtained by estimating a scattered X-ray image of the virtual model obtained by radiography from the virtual model, as an estimated image which is obtained by estimating a radiographic image of the subject obtained by radiography; a correction step of correcting the body thickness distribution of the virtual model such that a difference between the estimated image and the subject image is reduced; and a body thickness distribution determination step of determining the corrected body thickness distribution of the virtual model as the body thickness distribution of the subject.

In addition, a program may be provided which causes a computer to perform the radiographic image analysis method according to the above-mentioned aspect of the invention.

The "body thickness" means the sum of the thicknesses of subject regions other than air regions on an emitted radiation path.

The "estimated image" may be substantially regarded as a composite image of an estimated primary X-ray image, which is obtained by estimating a primary X-ray image of the virtual model obtained by radiography from the virtual model, and an estimated scattered X-ray image, which is obtained by estimating a scattered X-ray image of the virtual model obtained by radiography from the virtual model. For example, an estimated primary X-ray image generation function may be applied to the virtual model to generate the estimated primary X-ray image, an estimated scattered X-ray image generation function may be applied to the virtual model to generate the estimated scattered X-ray image, and the images may be combined with each other. In addition, an estimated image generation function may be applied to the virtual model to estimate the estimated image.

In the radiographic image analysis device according to the above-mentioned aspect of the invention, preferably, the virtual model acquisition unit further acquires the virtual model having the corrected body thickness distribution, the estimated image generation unit further generates the estimated image from the virtual model having the corrected body thickness distribution, and the correction unit further corrects the body thickness distribution of the virtual model such that a difference between the generated estimated image and the subject image is reduced.

In this case, preferably, when the difference between the estimated image and the subject image is equal to or less than a predetermined threshold value, the body thickness distribution determination unit determines the body thickness distribution of the virtual model as the body thickness distribution of the subject.

In the radiographic image analysis device according to the above-mentioned aspect of the invention, the correction unit may correct the body thickness distribution of the virtual model such that the sum of absolute values of pixel values of a difference image between the estimated image and the subject image or the sum of the squares of the pixel values of the difference image is reduced.

In the radiographic image analysis device according to the above-mentioned aspect of the invention, the correction unit may change the body thickness distribution of the virtual model for each partial region including one or more pixels in the virtual model, calculate a body thickness of the partial region at which the difference between the estimated image and the subject image is reduced, and correct the body thickness distribution of the virtual model using the calculated body thickness of each partial region.

In the invention, the "predetermined body thickness distribution" is not necessarily similar to the body thickness distribution of the subject and may be any body thickness distribution. For example, when the subject is a predetermined part of the human body, the predetermined body thickness distribution may be the body thickness distribution of the same part of a human body different from the subject or the predetermined body thickness distribution may be a uniform distribution.

In the radiographic image analysis device according to the above-mentioned aspect of the invention, the predetermined body thickness distribution may be created by acquiring a comparative subject image of a comparative subject different from the subject, which is obtained by radiography, and a three-dimensional image of the comparative subject obtained by three-dimensional imaging, and measuring a body thickness of the comparative subject on a straight line corresponding to a radiation path of the comparative subject image at each position of the acquired three-dimensional image.

In the radiographic image analysis device according to the above-mentioned aspect of the invention, preferably, the virtual model further includes characteristic information indicating at least one of structures included in the virtual model, the arrangement of the structures, and characteristics of the structures with respect to radiation, and the estimated image generation unit selects a parameter for calculating the estimated image according to the structure corresponding to each position of the virtual model, on the basis of the characteristic information, and generates the estimated image.

In the radiographic image analysis device according to the above-mentioned aspect of the invention, preferably, the estimated image generation unit acquires characteristic information indicating structures included in the subject image, the arrangement of the structures, and characteristics of the structures with respect to radiation as the characteristic information of the virtual model, selects a parameter for calculating the estimated image according to the structure corresponding to each position of the virtual model, on the basis of the characteristic information, and generates the estimated image.

The "characteristic information" may be specified by any method as long as it indicates the structures included in the image, the arrangement of the structures, and the characteristics of the structures with respect to radiation. For example, the characteristic information can be defined by the anatomic structures to be captured, such as the lung field, bone, blood vessel, and organ of the subject, and the composition of each anatomic structure.

Preferably, the radiographic image analysis device according to the above-mentioned aspect of the invention further includes: a scattered X-ray information acquisition unit that acquires scattered X-ray information which is obtained by estimating a scattered X-ray of the subject image, using the determined body thickness distribution of the subject; and a scattered X-ray removal unit that performs a process of removing the scattered X-ray of the subject image on the basis of the acquired scattered X-ray information.

In the above-mentioned aspects of the invention, the subject image may be captured without using a scattered X-ray removal grid.

According to the invention, the subject image is acquired. The virtual model of the subject having a predetermined body thickness distribution is acquired. The composite image of the estimated primary X-ray image, which is obtained by estimating the primary X-ray image of the virtual model obtained by radiography from the virtual model, and the estimated scattered X-ray image, which is obtained by estimating the scattered X-ray image of the virtual model obtained by radiography from the virtual model, is generated as the estimated image which is obtained by estimating the radiographic image of the subject obtained by radiography. The body thickness distribution of the virtual model is corrected such that the difference between the estimated image and the subject image is reduced. The corrected body thickness distribution of the virtual model is determined as the body thickness distribution of the subject. According to this structure, it is possible to correct the body thickness distribution on the basis of the difference between the estimated image and the subject image such that the estimated image is close to the subject image. Therefore, since the corrected body thickness distribution of the virtual model is determined as the body thickness distribution of the subject, it is possible accurately determine the body thickness distribution of the subject image.

In addition, the virtual model acquisition unit further acquires the virtual model having the corrected body thickness distribution, the estimated image generation unit further generates the estimated image from the virtual model having the corrected body thickness distribution, and the correction unit further corrects the body thickness distribution of the virtual model such that the difference between the generated estimated image and the subject image is reduced. In this case, the process of correcting the body thickness distribution on the basis of the virtual model having the corrected body thickness distribution is repeatedly performed to accurately correct the body thickness distribution such that the estimated image is close to the subject image. Since the corrected body thickness distribution of the virtual model is determined as the body thickness distribution of the subject, it is possible to more accurately determine the body thickness distribution of the subject image.

BRIEF DESCRIPTION OF THE DRAWINGS

FIG. 7 is a flowchart illustrating a process performed by a radiographic image analysis device according to a fourth embodiment of the invention.

FIG. 8 is a flowchart illustrating a process performed by a radiographic image analysis device according to a fifth embodiment of the invention.

DESCRIPTION OF THE PREFERRED EMBODIMENTS

Figure 1:
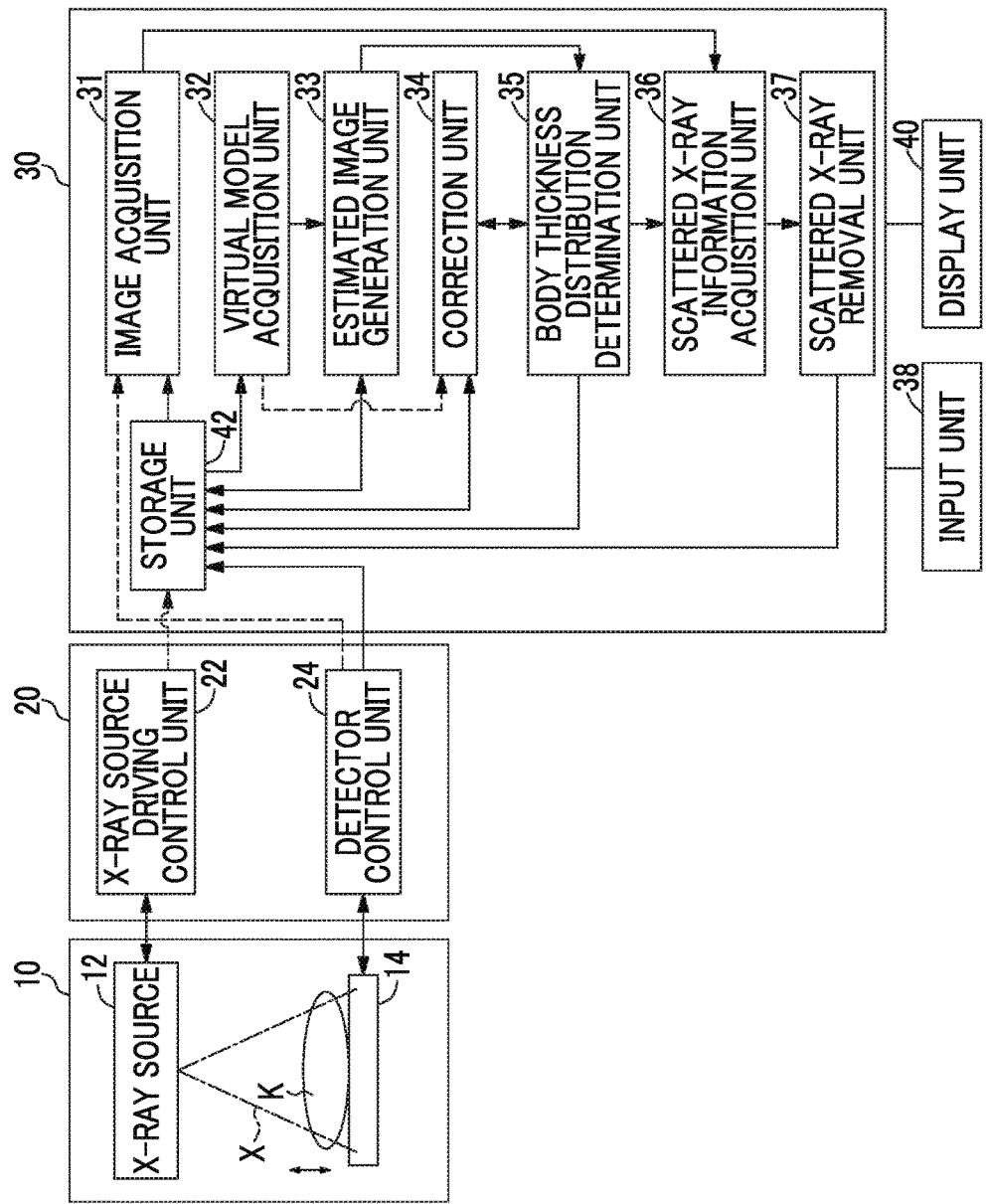
FIG. 1 is a block diagram schematically illustrating the structure of a radiography system to which a radiographic image analysis device according to a first embodiment of the invention is applied.

Hereinafter, embodiments of the invention will be described with reference to the drawings. FIG. 1 is a block diagram schematically illustrating the structure of a radiography system to which a radiographic image analysis device according to a first embodiment of the invention is applied. As illustrated in FIG. 1, the radiography system according to this embodiment includes an imaging device 10, a control device 20 which controls the system, and an image analysis device 30 (radiographic image analysis device).

The imaging device 10 includes an X-ray source 12 which irradiates a subject K with X-rays and a radiation detector 14 which detects X-rays passing through the subject K and acquires a radiographic image of the subject K. In this embodiment, a scattered X-ray removal grid (grid) for removing X-rays which are scattered by the subject K among the X-rays passing through the subject K is not provided between the subject K and the radiation detector 14.

The control device 20 includes an X-ray source driving control unit 22 which controls the driving of the X-ray source 12 according to set imaging conditions and a detector control unit 24 which controls the radiation detector 14 such that the radiographic image (subject image) of the subject is acquired and stores the radiographic image in a storage unit 42.

The image analysis device 30 includes an image acquisition unit 31 which acquires a captured subject image Ik of the subject K from, for example, the detector control unit 24 or the storage unit 42, which will be described below, a virtual model acquisition unit 32 which acquires a virtual model M of the subject K having an initial body thickness distribution $T_0$ (predetermined body thickness distribution), an estimated image generation unit 33 which generates a composite image of an estimated primary X-ray image Ip, which is obtained by estimating a primary X-ray image of the virtual model obtained by radiography from the virtual model M, and an estimated scattered X-ray image Is, which is obtained by estimating a scattered X-ray image of the virtual model obtained by radiography from the virtual model M, as an estimated image Im which is obtained by estimating the radiographic image of the subject K obtained by radiography, a correction unit 34 which corrects the initial body thickness distribution $T_0$ of the virtual model M such that the difference between the estimated image Im and the subject image Ik is reduced, on the basis of the estimated image Im and the subject image Ik, a body thickness distribution determination unit 35 which determines the corrected body thickness distribution $T_{n-1}$ (n is a natural number) as a body thickness distribution Tk of the subject image Ik, a scattered X-ray information acquisition unit 36 which acquires scattered X-ray information indicating a scattered X-ray component of the X-ray included in the subject image Ik on the basis of the determined body thickness distribution Tk(x, y), a scattered X-ray removal unit 37 which performs a process of removing the scattered rays of the subject image Ik acquired by the radiation detector 14 on the basis of the scattered X-ray information acquired by the scattered X-ray information acquisition unit 36, an input unit 38, a display unit 40, and a storage unit 42 which includes storage media, such as a memory and a hard disk, and stores various kinds of information. The input unit 38 receives various inputs of the operator to the image analysis device 30. Specifically, the input unit 38 is, for example, a keyboard, a mouse, or a touch panel. The display unit 40 is, for example, a CRT display or a liquid crystal display and assists the display of the radiographic image acquired by the imaging device 10 and various inputs required for a scattered X-ray removal process which will be described below.

The image acquisition unit 31, the virtual model acquisition unit 32, the estimated image generation unit 33, the correction unit 34, the body thickness distribution determination unit 35, the scattered X-ray information acquisition unit 36, the scattered X-ray removal unit 37, the input unit 38, the display unit 40, and the storage unit 42 can be formed by a computer system such as a general personal computer.

The image analysis device 30 analyzes the subject image Ik which has been captured by the irradiation of the subject K, who is the person to be examined, with radiation to estimate the body thickness distribution Tk of the subject K.

The storage unit 42 of the image analysis device 30 stores imaging conditions such as the subject image Ik acquired by the detector control unit 24, the radiography dose thereof, a tube voltage, a distance SID between the X-ray source 12 and a detection surface of the radiation detector 14, materials forming the object to be irradiated by the X-ray source and a filter, the type of radiation detector used for radiography, and an air gap (the distance from the subject to the radiation detector). An association table LUT in which a concentration value (pixel value) and a body thickness are associated with each other for each of a plurality of imaging conditions is created in advance and is stored in the storage unit 42. In addition, the storage unit 42 stores the virtual model M of the subject K having the initial body thickness distribution $T_0$(x, y). It is assumed that various parameters required for each process and the generated images (for example, the estimated primary X-ray image and the estimated scattered X-ray image) are appropriately stored in the storage unit 42. In the specification, the body thickness means the sum of the thicknesses of subject regions except for an air region on the path of the emitted radiation. In this embodiment, the detector control unit 24 acquires the imaging conditions and stores the imaging conditions in the storage unit 42. However, the X-ray source driving control unit 22 may acquire the imaging conditions and store the imaging conditions in the storage unit 42.

Next, the flow of a radiographic image analysis process performed by the image analysis device 30 according to this embodiment will be described with reference to the flowchart illustrated in FIG. 2.

First, the image acquisition unit 31 acquires the subject image Ik of a patient, who is the subject K, obtained by radiography from the storage unit 42 (S01).

Then, the virtual model acquisition unit 32 acquires the virtual model M of the subject K having the initial body thickness distribution $T_0$(x, y) from the storage unit 42 (S02). The virtual model M is data which virtually indicates the subject K having the initial body thickness distribution $T_0$(x, y) in which the body thickness is associated with each position on an x-y plane. Structures (here, anatomic structures such as a lung field, a bone, and an organ) included in the virtual model M, the arrangement of the structures, and characteristic information indicating, for example, the characteristics of the structures with respect to radiation are set on the basis of the arrangement and composition of anatomic structures, such as the lung field of the chest and abdomen of a comparative subject and the bones in the vicinity thereof.

Figure 3:
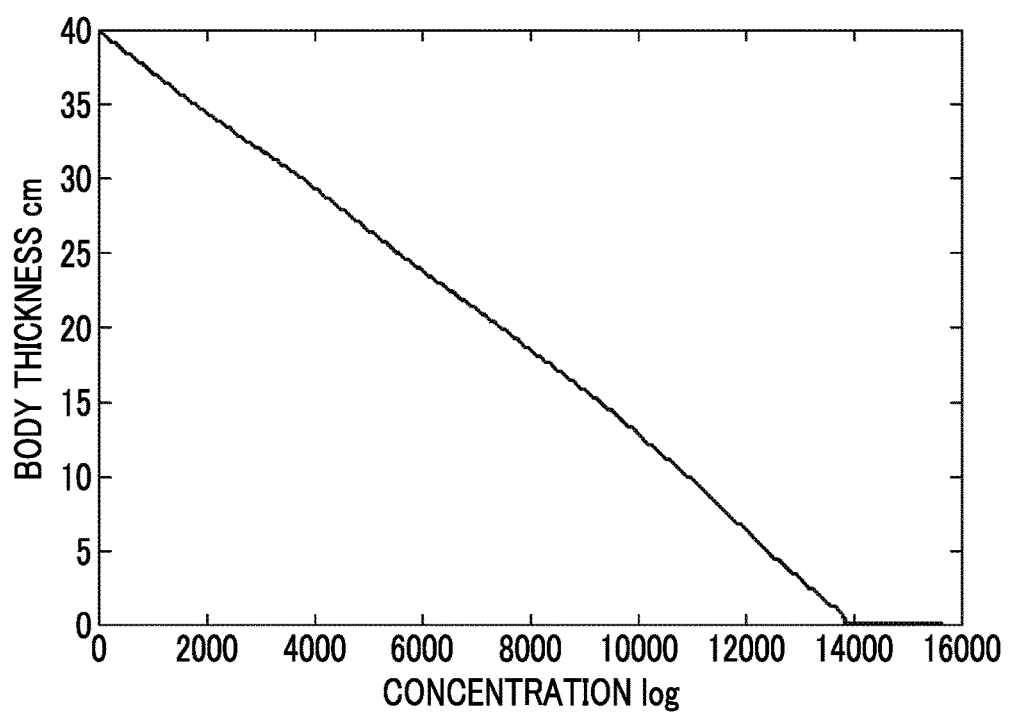
FIG. 3 is a diagram illustrating an example of an association table of a body thickness distribution.

The virtual model M may have any initial body thickness distribution $T_0$(x, y). However, in this embodiment, the initial body thickness distribution $T_0$ is generated and acquired by the virtual model acquisition unit 32. The virtual model acquisition unit 32 acquires the imaging conditions, such as the radiography dose of the subject K, a tube voltage, and an SID, and acquires an association table LUT in which the pixel value corresponding to the imaging conditions of the subject K is associated with the body thickness from the storage unit 42. FIG. 3 illustrates an example of the table LUT in which the pixel value is associated with the body thickness. Then, the virtual model acquisition unit 32 acquires the image data of the comparative subject (human body) obtained by radiography from the storage unit 42 and specifies the body thickness corresponding to the value of each pixel in the image data of the comparative subject on the basis of the association table LUT to acquire a body thickness distribution of the image data of the comparative subject. Then, the virtual model acquisition unit 32 acquires the body thickness distribution of the image data as the initial body thickness distribution $T_0$ (predetermined body thickness distribution) of the virtual model M. The initial body thickness distribution $T_0$ may be generated during the process of acquiring the virtual model M as in this embodiment, or may be set before the process of acquiring the virtual model M.

$$T_0(x,y)=LUT(I_k(x,y)) \quad (1)$$

Figure 4A:
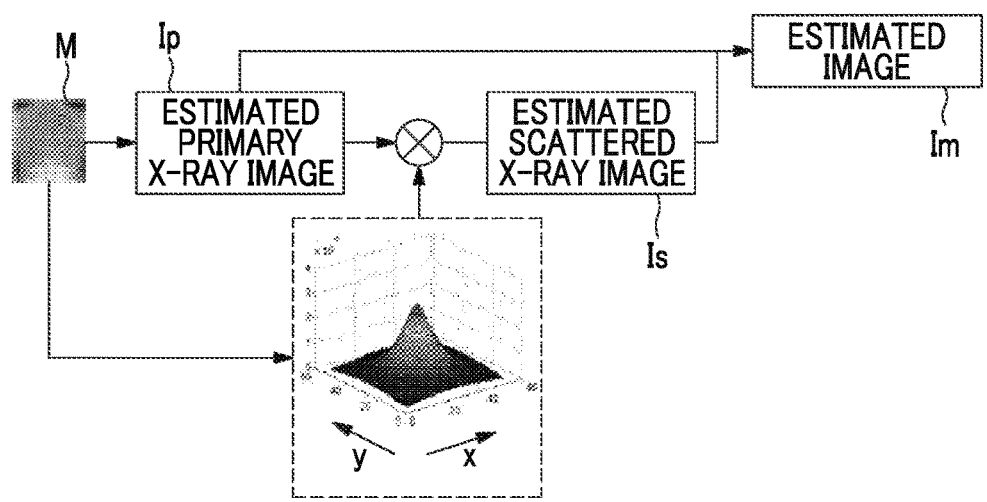
FIG. 4A is a diagram illustrating an example of an estimated image generation method.
Figure 4B:
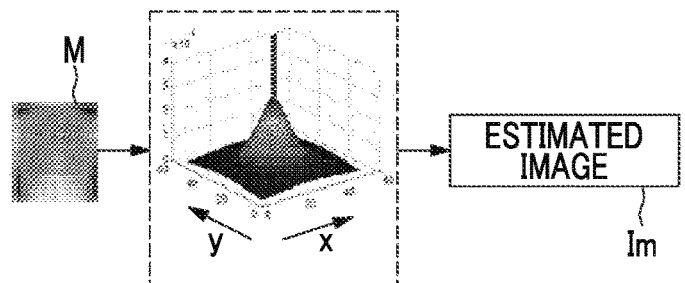
FIG. 4B is a diagram illustrating another example of the estimated image generation method.

Then, the estimated image generation unit 33 combines the estimated primary X-ray image Ip, which is obtained when the image of the virtual model M is captured under the same imaging conditions as the subject image, and the estimated scattered X-ray image Is, which is obtained when the image of the virtual model M is captured under the same imaging conditions as the subject image, to generate the estimated image Im (S03). FIGS. 4A and 4B are diagrams illustrating a method for generating the estimated image Im.

As illustrated in FIG. 4A, the estimated image generation unit 33 generates the estimated primary X-ray image Ip, which is obtained when the image of the virtual model M is captured under the same imaging conditions as the subject image Ik, according to the following Expression (2), and generates the estimated scattered X-ray image Is using the generated estimated primary X-ray image Ip, according to the following Expression (3). Then, the estimated image generation unit 33 combines the estimated primary X-ray image Ip and the estimated scattered X-ray image Is to generate the estimated image Im, as shown in the following Expression (4) (S03). When the estimated primary X-ray image Ip and the estimated scattered X-ray image Is are generated first, the initial body thickness distribution $T_0(x, y)$ is used in Estimation Expressions (2) and (3) (n is 1 in Expressions (2) and (3)).

$$I_p(x, y) = I_o(x, y) \times \exp(-T_{n-1}(x, y) \times \mu) \quad (2)$$

$$I_s(x, y) = \sum_{x',y'} I_p(x', y') K_s(x, y, T_{n-1}(x', y'), \theta_{x',y'}) \quad (3)$$

$$I_m(x, y) = I_p(x, y) + I_s(x, y) \quad (4)$$

Here, (x, y) is the coordinates of a pixel position of the subject image Ik, Ip(x, y) is an estimated primary X-ray image at the pixel position (x, y), Is(x, y) is an estimated scattered X-ray image at the pixel position (x, y), Io(x, y) is a dose at the pixel position (x, y), Im(x, y) is an estimated image at the pixel position (x, y), μ is a linear attenuation coefficient of the subject, and $K_s(x, y, T_n(x', y'), \theta_{x', y'})$ is a convolution kernel indicating a point spread function corresponding to the thickness of the subject at the pixel position (x, y). The dose Io(x, y) is a radiation dose which is detected by a detector on the assumption that no subject is present and varies depending on the distance (SID) between the X-ray source 12 and the detection surface of the radiation detector 14, a tube voltage, and a radiography dose. In addition, $\theta_{x', y'}$ indicates a parameter which is specified by the imaging conditions, such as the tube voltage, or the characteristic information of the virtual model M.

In addition, the estimated image Im may be an image which is estimated to be obtained when the radiographic image of the virtual model M is captured and may be any image which is substantially regarded as a composite image of the estimated primary X-ray image Ip and the estimated scattered X-ray image Is. For example, as illustrated in FIG. 4B, the estimated image Im may be generated by the convolution integral of the kernel combining a primary X-ray component and a scattered X-ray component, using the following Expression (5), instead of Expressions (2) to (4). Here, $K_{p+s}(x, y, T_{n-1}(x', y'), \theta_{x', y'})$ is a kernel indicating a point spread function that combines the primary X-ray component and the scattered X-ray component. In addition, any model function may be used as long as it can generate an estimated image obtained by combining the estimated primary radiation image and the estimated scattered X-ray image from the image obtained by radiography.

$$I_m(x, y) = \sum_{x',y'} K_{p+s}(x, y, T_{n-1}(x', y'), \theta_{x',y'}) \quad (5)$$

The next process will be described with reference to the flowchart illustrated in FIG. 2. Then, the body thickness distribution determination unit 35 determines whether the difference between the subject image Ik and the estimated image Im satisfies end conditions (S04). Here, an error value $V_{error}$ indicating the difference between the subject image Ik and the estimated image Im is defined as shown in the following Expression (6) and Expression (7). It is determined whether the error value $V_{error}$ is equal to or less than a threshold value as the end conditions. As shown in Expression (7), the sum of the squares of each pixel value of a difference image Id which is obtained by subtracting the estimated image Im from the subject image Ik is defined as the error function $f_{error}$. In addition, any determination method may be used as long as it can determine whether or not the difference between the subject image Ik and the estimated image Im is small enough to be allowable, as the end conditions.

$$V_{error} = f_{error}(I_m(x, y), I_k(x, y)) \quad (6)$$

$$f_{error}(I_m(x, y), I_k(x, y)) = \sum_{x,y} (I_m(x, y) - I_k(x, y))^2 \quad (7)$$

However, the invention is not limited to the above-mentioned example. For example, the error function $f_{error}$ can be defined by any method which can indicate the difference between the subject image Ik and the estimated image Im. For example, as shown in the following Expression (8), the sum of the absolute values of each pixel value of a differential image Id obtained by subtracting the estimated image Im from the subject image Ik may be defined as the error function $f_{error}$.

$$f_{error}(I_m(x, y), I_k(x, y)) = \sum_{x,y} |I_m(x, y) - I_k(x, y)| \quad (8)$$

When the error value $V_{error}$ does not satisfy the end conditions (S04, No), the correction unit 34 performs a correction process of correcting a body thickness distribution $T_{n-1}$ (the initial body thickness distribution $T_0$ when n is 1) (S05).

Any method which can acquire the correction value of each position in the body thickness distribution $T_{n-1}$ such that the difference between the subject image Ik and the estimated image Im is reduced can be applied in order to perform the process of correcting the body thickness distribution $T_{n-1}$. In this embodiment, a process is performed which changes the body thickness distribution $T_{n-1}$ of the virtual model M for each partial region including one or more pixels in the virtual model M to calculate the body thickness of the partial region where the difference between the estimated image Im and the subject image Ik is small. Then, the body thickness distribution of the virtual model is corrected by the calculated body thickness of each partial region.

Specifically, in this embodiment, it is assumed that the correction value of the body thickness with the body thickness distribution $T_{n-1}$ is calculated using the steepest descent method. It is possible to minimize the output value of the error function $f_{error}$ by repeatedly calculating $dT_{n-1}(x, y)$ on the basis of the primary partial differential (gradient) of the error function $f_{error}$ while changing only the body thickness at one specific coordinate point in $T_{n-1}(x, y)$ among the pixels of the virtual model M, using the following Expressions (9) and (10). Then, the body thickness at one specific coordinate point when the output value of the error function $f_{error}$ is minimized is determined as the correction value of the body thickness at the coordinate point. For the other pixels, similarly, the correction value of each body thickness is calculated and the body thickness distribution of each pixel is corrected. In this way, a corrected body thickness distribution Tn is acquired.

$$T_n(x, y) = T_{n-1}(x, y) - \alpha dT_{n-1}(x, y) \quad (9)$$
$$= T_{n-1}(x, y) - \alpha \frac{d}{dT_{n-1}(x, y)} f_{error}$$

$$\frac{d}{dT_{n-1}(x, y)} f_{error} = \quad (10)$$
$$\sum_{x',y'} (I_m(x', y') - I_k(x', y')) \frac{d}{dT_{n-1}(x, y)} K_{p+s}(x', y', T_{n-1}(x, y), \theta_{x,y})$$

$$\frac{d}{dT_{n-1}(x, y)} K_{p+s}(x', y', T_{n-1}(x, y), \theta_{x,y}) = \quad (11)$$
$$K_{p+s}(x', y', T_{n-1}(x, y) + dt, \theta_{x,y}) - K_{p+s}(x', y', T_{n-1}(x, y), \theta_{x,y})$$

However, in Expression (9), α is an update coefficient which is a parameter indicating the update speed of the body thickness. As an example of a method for calculating a differential value portion of $K_{p+s}$ shown in Expression (10), for example, a value change when a very small value dt is added to $T_{n-1}(x, y)$ can be calculated by Expression (11) and can be used as the value of $K_{p+s}$ in the Expression (10). In Expressions (1) to (12), the same components are denoted by the same reference numerals and the description thereof will not be repeated. Any optimization method can be applied as long as it can minimize the error value $V_{error}$ indicating the difference between the subject image Ik and the estimated image Im. For example, a simplex method, the steepest descent method, or a conjugate gradient method can be used.

When the corrected body thickness distribution $T_n$ is acquired, the body thickness distribution determination unit 35 increases the value of n by 1 to update the value of n (n=n+1) and the virtual model acquisition unit 32 acquires the corrected body thickness distribution $T_n$ (S02). Then, the estimated image generation unit 33 and the body thickness distribution determination unit 35 perform the process in S03 and S04 for the acquired body thickness distribution $T_n$ using the same method as described above. Then, similarly, the process of correcting the body thickness distribution $T_n$ (S05), the process of acquiring the virtual model M having the corrected body thickness distribution $T_n$ (S02), the process of generating a new estimated image Im using the body thickness distribution $T_n$ (S03), and the process of determining whether the difference between a newly generated estimated image Im and the subject image Ik satisfies the end conditions (S04) are repeatedly performed until the error value $V_{error}$ indicating the difference between the subject image Ik and the estimated image Im satisfies the end conditions.

On the other hand, if it is determined that the error value $V_{error}$ satisfies the end conditions (S04, Yes), the body thickness distribution determination unit 35 determines the body thickness distribution $T_n$ used for the error value $V_{error}$ when the end conditions are satisfied as the body thickness distribution Tk of the subject image Ik and ends the image analysis process according to this embodiment (S06).

In this embodiment, when an instruction to perform a scattered X-ray removal process for the subject image Ik is received from the user after the body thickness distribution determination process (S06) illustrated in FIG. 3, a scattered X-ray information acquisition process and the scattered X-ray removal process are performed as optional functions of the image analysis device 30. Here, the scattered X-ray information acquisition unit 36 applies the acquired body thickness distribution Tk, acquires an estimated primary X-ray image of the subject image Ik according to Expression (2), and acquires an estimated scattered X-ray image Is(x, y) of the subject image Ik(x, y) according to Expression (3). Then, the scattered X-ray removal unit 37 subtracts the estimated scattered X-ray image Is(x, y) of the subject image Ik from the subject image Ik(x, y) to generate a processed image from which the influence of scattered rays has been removed and stores the processed image in the storage unit 42. The processed image is appropriately displayed on the display unit 40 in response to an instruction from the user. In the determination of the end conditions (S04), when the error value $V_{error}$ satisfies the end conditions, the difference between the subject image Ik and the estimated image Im is small enough to be allowable and the difference between the estimated primary X-ray image Ip and the primary X-ray image of the subject image Ik is also small. Therefore, when the user wants to acquire the processed image, from which the scattered rays have been removed, from the subject image Ik, the estimated primary X-ray image Ip used to calculate the error value $V_{error}$ satisfying the end conditions may be acquired as the primary X-ray image of the subject image Ik, that is, a processed image after the process of removing scattered rays from the subject image Ik.

According to this embodiment, the estimated primary X-ray image Ip and the estimated scattered X-ray image Is of the virtual model M which are estimated to be obtained by radiography are combined to generate the estimated image Im and the body thickness distribution of the virtual model M is corrected such that the difference between the estimated image Im and the subject image Ik is reduced. Therefore, it is possible to accurately correct the body thickness distribution $T_n$ on the basis of the difference between the estimated image Im and the subject image Ik such that the estimated image Im is close to the subject image Ik. The corrected body thickness distribution $T_n$ of the virtual model M is used as the body thickness distribution Tk of the subject K, which makes it possible to accurately determine the body thickness distribution Tk of the subject image Ik. In the method according to the related art, the influence of the scattered X-ray component is large in the image which is captured without using a grid and it is difficult to accurately calculate the body thickness distribution from the image. In contrast, the method according to this embodiment accurately corrects the body thickness distribution $T_n$ such that the estimated image Im is close to the subject image Ik and determines the corrected body thickness distribution as the body thickness distribution Tk of the subject K. Therefore, even when the subject image Ik is captured without using a grid, it is possible to more accurately obtain the body thickness distribution Tk than the method according to the related art.

In addition, as described in this embodiment, the virtual model acquisition unit 32 further acquires the virtual model M having the corrected body thickness distribution $T_n$ and the estimated image generation unit 33 further generates the estimated image Im from the virtual model M having the corrected body thickness distribution $T_n$. When further correcting the body thickness distribution $T_n$ of the virtual model M such that the difference between the generated estimated image Im and the subject image Ik is reduced, the correction unit 34 repeatedly performs the process of correcting the body thickness distribution T on the basis of the virtual model having the corrected body thickness distribution $T_n$ to accurately correct the body thickness distribution T such that the estimated image Im is close to the subject image Ik. Therefore, since the corrected body thickness distribution $T_{n+1}$ of the virtual model M is used as the body thickness distribution Tk of the subject K, it is possible to accurately determine the body thickness distribution Tk of the subject image Ik.

As described in this embodiment, when the difference between the estimated image Im and the subject image Ik is small enough to be allowable, the body thickness distribution determination unit 35 determines the body thickness distribution $T_n$ of the virtual model M as the body thickness distribution Tk of the subject K. In this case, the body thickness distribution is repeatedly corrected such that the estimated image Im is close to the subject image Ik. Therefore, it is possible to very accurately determine the body thickness distribution of the subject image. In addition, the body thickness distribution determination unit 35 determines whether or not the difference between the estimated image Im and the subject image Ik is equal to or less than the threshold value. Therefore, the body thickness distribution determination unit 35 appropriately determines whether the difference between the estimated image Im and the subject image Ik is small enough to be allowable and repeatedly corrects the body thickness distribution such that the estimated image Im is close to the subject image Ik. As a result, it is possible to very accurately determine the body thickness distribution of the subject image.

In this embodiment, the correction unit 34 corrects the body thickness distribution of the virtual model such that the sum of the absolute values of the pixel values of a difference image between the estimated image and the subject image or the sum of the squares of the pixel values of the difference image is reduced. Therefore, it is possible to appropriately determine the magnitude of the difference between the estimated image Im and the subject image Ik.

As described in this embodiment, the correction unit 34 changes the body thickness of one partial region in the body thickness distribution $T_{n-1}$ of the virtual model M for each partial region including one or more pixels in the virtual model M and calculates the body thickness of the one part when the difference between the estimated image Im and the subject image Ik is minimized. In addition, the correction unit 34 corrects the body thickness distribution of the virtual model M using the calculated body thickness of each part. Therefore, it is possible to accurately calculate the correction value of the body thickness of each pixel and to acquire an appropriately corrected body thickness distribution $T_n$.

According to this embodiment, the image analysis device includes the scattered X-ray information acquisition unit 36 which acquires scattered X-ray information obtained by estimating the scattered rays of the subject image using the determined body thickness distribution Tk of the subject K and the scattered X-ray removal unit 37 which performs the process of removing the scattered rays of the subject image on the basis of the acquired scattered X-ray information. Therefore, it is possible to acquire a processed image subjected to the scattered X-ray removal process with high accuracy.

In a second embodiment of the invention, the estimated image generation unit 33 may acquire structures included in the subject image Ik, the arrangement of the structures, and characteristic information indicating the characteristics of the structures with respect to radiation as the characteristic information of the virtual model M, select parameters for calculating the estimated image Im according to the structure corresponding to each position of the virtual model M, on the basis of the characteristic information, and generate the estimated image Im. For example, it is considered that, as shown in the following Expression (12), the linear attenuation coefficient in Expression (2) when the estimated primary X-ray image Ip is generated from the virtual model M using Expression (2) is changed at each position depending on the structures (the composition of the structure), on the basis of the characteristic information, and is then used. In a radiographic image, a primary X-ray component or a scattered X-ray component is complexly changed at each position on the radiographic image, depending on the structures included in the subject, such as the bone of the subject, the kind of organ, and a cavity included in the organ, and the spatial position of the structures. Therefore, when the characteristic information of the subject image Ik is acquired as the characteristic information of the virtual model M and the parameters used for, for example, the estimated primary X-ray image or the estimated scattered X-ray image are appropriately selected according to the structure (virtually) included at each position of the virtual model M, it is possible to reduce errors of the primary X-ray component or the scattered X-ray component caused by the structure and to accurately generate the estimated primary X-ray image Ip and the estimated scattered X-ray image Is.

$$\mu(x, y) = \begin{cases} \mu_{bone} & \text{when a bone is present at the position} \\ \mu_{lung} & \text{when the lung is present at the position} \\ \mu_{soft} & \text{when a soft tissue is present at the position} \end{cases} \quad (12)$$

For the parameter $\theta_{x',y'}$ of $K_s$ in Expression (3), different values of $\theta_{x',y'}$ may be set for each structure and $\theta_{x',y'}$ applied to each position may vary depending on the structure at each position. In addition, a three-dimensional image, such as a CT image or an MRI image of the same subject K as that in the subject image Ik, may be acquired, and the characteristic information of the subject image Ik may be measured and acquired from the acquired CT image or MRI image. When characteristic information is acquired using the three-dimensional image of the same subject K, it is possible to accurately acquire information such as the spatial position of the organ or the bone.

Various body thickness distributions may be used as the initial body thickness distribution (predetermined body thickness distribution). For example, the initial body thickness distribution may be a uniform distribution. However, it is preferable to use the body thickness distribution which is estimated to be close to the subject K to a certain extent as the initial body thickness distribution in terms of a calculation load. From this point of view, for example, it is preferable that the body thickness distribution T previously measured for the same subject K is used as the initial body thickness distribution $T_0$. In this case, it is possible to determine the body thickness distribution only by finely correcting a difference in the subject K due to a posture or a change over time and to reduce a calculation load.

In addition, the initial body thickness distribution $T_0$ may be created by acquiring a comparative subject image of a comparative subject different from the subject, which is obtained by radiography, and a three-dimensional image, such as a CT image or an MRI image obtained by a three-dimensional imaging process for the comparative subject, and by measuring the body thickness of the comparative subject on a straight line corresponding to a radiation path in the comparative subject image at each position on the acquired three-dimensional image. The use of the three-dimensional image makes it possible to obtain an accurate initial body thickness distribution. Therefore, it is possible to determine the body thickness distribution only by finely correcting, for example, the posture of the subject and thus to reduce a calculation load.

When the body thickness distribution of the comparative subject is prepared, the following is considered: a plurality of sets of the body thickness distribution of each comparative subject and physique information indicating the physique of the comparative subject are prepared for a plurality of comparative subjects; the physique information of the subject is acquired; the body thickness distribution of the comparative subject having the physique information similar to the physique information of the subject is specified; and the specified body thickness distribution of the comparative subject is used as the initial body thickness distribution $T_0$ of the subject image. In this case, since the body thickness distribution of the comparative subject having a similar physique to the subject is used as the initial body thickness distribution, the initial body thickness distribution is likely to be similar to the body thickness distribution of the subject and it is possible to determine the body thickness distribution only by finely correcting, for example, the posture of the subject and thus to reduce a calculation load. In addition, the physique information of the subject and the physique information of the comparative subject may be input by the user, or may be physique information extracted from the subject image and the comparative subject, such as the width of the concentration histogram of each of the subject image and the radiographic image of the comparative subject (the difference between the maximum value and the minimum value of a concentration value). Furthermore, any physique information may be used as long as it can be extracted from the subject image and the comparative subject. For example, the length of a predetermined part of the subject may be used as the physique information of the subject.

In addition, for example, the following method may be used: before and after the radiographic image of the subject is captured, the distance between the detector and the surface of the subject close to the X-ray source is measured by a measurement device, such as an ultrasonic sensor or a digital measurement device capable of measuring a distance; the measured value is acquired from, for example, the measurement device or the input of the user; and the acquired distance between the body surface of the subject and the detector is used as an index value for determining the initial body thickness distribution. In this case, for example, the distance between the body surface of the subject and the detector can be used as the physique information of the subject. In addition, the initial body thickness distribution may be a uniform distribution of the distance between the body surface of the subject and the detector.

Various methods which can generate the estimated primary X-ray image Ip and the estimated scattered X-ray image Is may be applied. For example, instead of Expressions (2) and (3), for example, a Monte Carlo simulation method may be used to generate the estimated primary X-ray image Ip and the estimated scattered X-ray image Is, as described in Kato Hideki, "A New Method for Eliminating Scatter Components from a Digital X-ray Image by Later Processing", Japanese Journal of Radiological Technology, Vo. 62, No. 9, September 2006, p. 1359-1368. In addition, when the Monte Carlo simulation method is used, it is preferable to use characteristic information which is information indicating structures included in the virtual model M, the arrangement of the structures, and the characteristics of the structures with respect to radiation. In this case, it is possible to generate the estimated primary X-ray image Ip and the estimated scattered X-ray image Is with higher accuracy.

In each of the above-described embodiments, the image analysis device may further include a imaging condition acquisition unit which acquires the actual imaging conditions that are considered to be used. The tube voltage, the radiography dose, and the distance SID between the X-ray source and the detector are changed depending on, for example, the body type of the subject, the purpose of diagnosis, or the environment of the facilities in which the radiography system is installed. Therefore, preferably, the imaging condition acquisition unit acquires the imaging conditions of the subject image Ik and the estimated image generation unit 33 selects a parameter (for example, $\theta_{x',y'}$ in Expressions (3) and (5)), which is used to generate the estimated image Im and varies depending on the imaging conditions, on the basis of the acquired imaging conditions and performs the process of generating the estimated image Im (S03) using the selected parameter.

The imaging condition acquisition unit may acquire the imaging conditions using any method as long as it can acquire the imaging conditions. For example, the imaging condition acquisition unit may acquire the imaging conditions which are input by the user or the imaging conditions which are calculated from the pixel value detected by the detector at the position where no subject is present. In this case, a table in which the concentration value of a void region, which is a region in which no subject is present, is associated with a radiography dose may be stored in the storage unit 42 and the radiography dose may be acquired with reference to the table on the basis of the concentration value of the void region. In addition, the imaging condition acquisition unit can use various methods which can acquire the imaging conditions actually applied to the capture of the subject image.

For example, the imaging condition acquisition unit may acquire the distance SID between the X-ray source and the surface of the detector using any method. For example, the imaging condition acquisition unit can acquire, as the SID, the distance between the X-ray source and the detector measured by a measurement device capable of measuring the distance, such as an ultrasonic sensor or a digital measure. In addition, the imaging condition acquisition unit may acquire a radiographic image of a three-dimensional marker which is arranged at the position that is a known distance away from the radiation detector 14 between the X-ray source 12 and the radiation detector 14 and analyze the position of the three-dimensional marker or a scattered X-ray component in the radiographic image to calculate the SID.

The imaging condition acquisition unit may acquire the radiography dose using any method. For example, the imaging condition acquisition unit may acquire a dose which is measured by a measurement device, such as an area dosimeter, as the radiography dose incident on the radiation detector 14. In addition, the imaging condition acquisition unit may capture the image of an acrylic model with a known thickness together with the image of the subject and acquire a radiography dose on the basis of the concentration of the acrylic model in the acquired radiographic image. In this case, a table in which the concentration of the acrylic model is associated with the radiography dose may be stored in the storage unit 42 and the radiography dose may be acquired with reference to the table on the basis of the concentration of the acrylic model. In many cases, the imaging conditions are determined according to the facilities in which the radiography system is installed. Therefore, when the imaging conditions are unclear in the actual radiography, it is preferable to use the imaging conditions corresponding to the facilities.

The pixel value of the subject image Ik is likely to vary depending on the type of radiation detector 14. Preferably, information for specifying the type of radiation detector 14 is included in the imaging conditions and a dose specification table in which a concentration value (pixel value) that is measured in advance is associated with a dose that reaches the radiation detector 14 is made for each combination of the radiography dose, the tube voltage, the SID, and the type of radiation detector 14 in advance and is then stored in the storage unit 42. In this case, the imaging condition acquisition unit may acquire the type of radiation detector 14 used to capture the subject image Ik, specify a dose corresponding to a concentration value at each position with reference to the dose specification table corresponding to the acquired type of radiation detector 14, and use the specified dose as the radiography dose.

Preferably, the correction unit 34 selects a parameter (for example, $\theta_{x',y'}$ in Expressions (10) and (11)), which is used to generate the estimated image Im and varies depending on the imaging conditions, on the basis of the acquired imaging conditions and performs the process of correcting the body thickness distribution of the estimated image Im (S05) using the selected parameter. In this case, it is possible to appropriately set the parameter which varies depending on the imaging conditions according to the imaging conditions of the subject image Ik and to generate the estimated image Im. Therefore, it is possible to accurately estimate and generate the estimated image Im. As a result, it is possible to accurately determine the body thickness distribution of the subject K.

In each of the above-described embodiments, the image acquisition unit 31 acquires the subject image Ik which is captured without using a grid. However, the invention is not limited thereto. The image acquisition unit 31 may acquire, as the subject image Ik, an image obtained by performing a process of removing a fringe caused by a grid for the radiographic image of the subject K which has been captured using the grid. The process of removing the fringe caused by the grid may be performed using various methods capable of removing the fringe caused by the grid. For example, the method disclosed in JP2012-203504A can be referred to.

When the image acquisition unit 31 acquires, as the subject image Ik, the image obtained by performing the process of removing the fringe caused by the grid for the radiographic image of the subject K which has been captured using the grid, it is preferable that a table in which scattered X-ray transmissivity Ts and primary X-ray transmissivity Tp are associated with each other for each grid information item for specifying the type of grid is made in advance and is then stored in the storage unit 42. In this case, it is preferable that the estimated image generation unit 33 specifies scattered X-ray transmissivity $Ts^k$ and primary X-ray transmissivity $Tp^k$ corresponding to grid information which is used to capture the image of the subject, on the basis of the table in which the scattered X-ray transmissivity Ts and the primary X-ray transmissivity Tp are associated with each grid information item, and generates the estimated image, using the following Conditional Expression (4-1) instead of Condition Expression (4). In this case, the absorption of primary rays by the same type of grid as that used to capture the subject image can be reflected in the estimated primary X-ray image of the virtual model and the absorption of scattered X-rays by the same type of grid as that used to capture the subject image can be reflected in the estimated scattered X-ray image of the virtual model. As such, since the absorption of the scattered X-rays and the primary X-rays by the same type of grid is reflected in the estimated image on the basis of the grid used to capture the subject image, it is possible to reduce errors in the body thickness distribution due to the absorption of radiation to the grid used to capture the subject image. The grid information can be any combination of a grid ratio, grid density, information indicating whether the grid is a convergence type or a parallel type, a focusing distance when the grid is a convergence type, and one or more elements included in an interspace material (for example, aluminum, fiber, or Bakelite).

$$I_m(x,y)=I_p(x,y)\times T_p^k+I_s(x,y)\times T_s^k \qquad (4\text{-}1)$$

Figure 5:
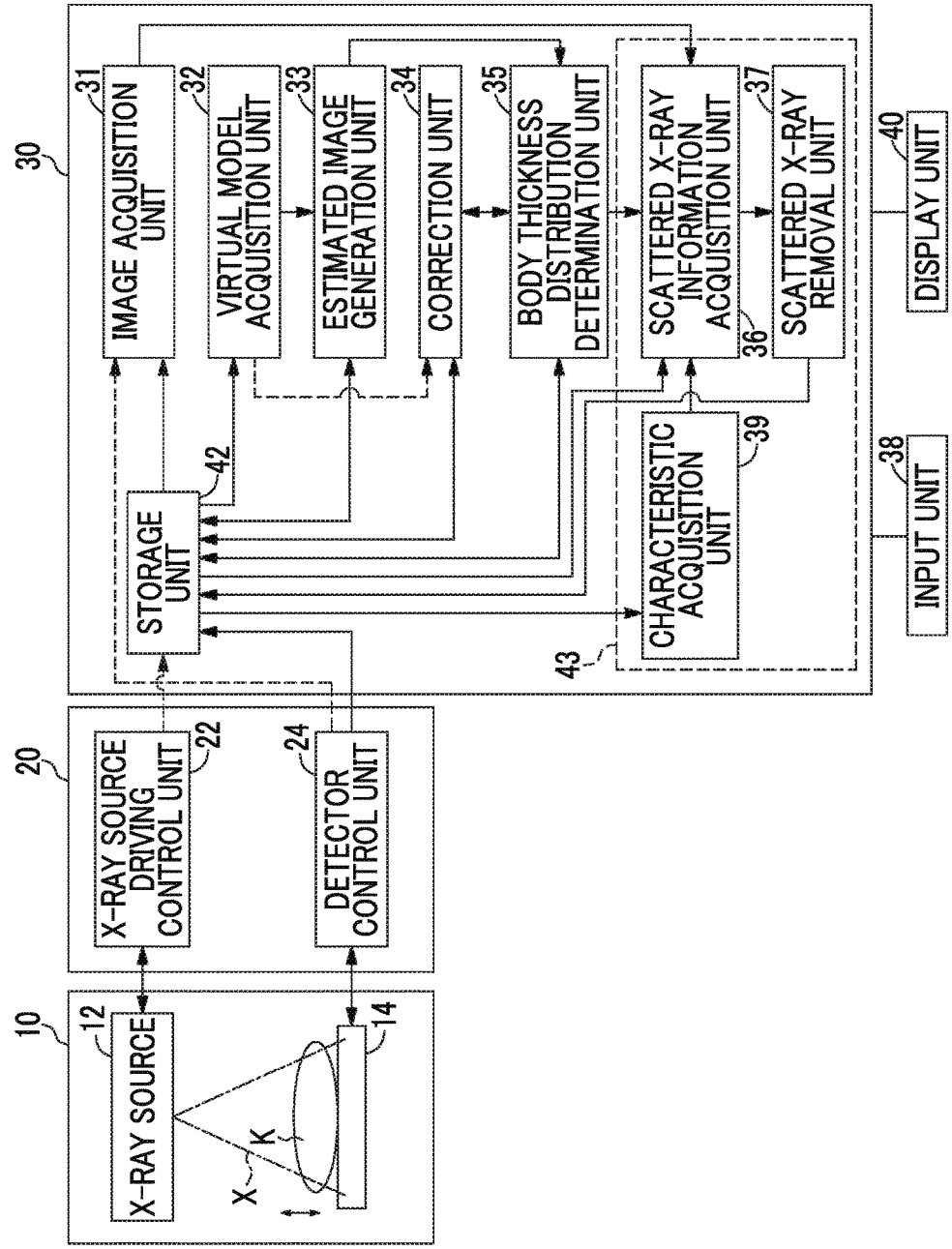
FIG. 5 is a block diagram schematically illustrating the structure of a radiography system to which a radiographic image analysis device according to a third embodiment of the invention is applied.
Figure 6:
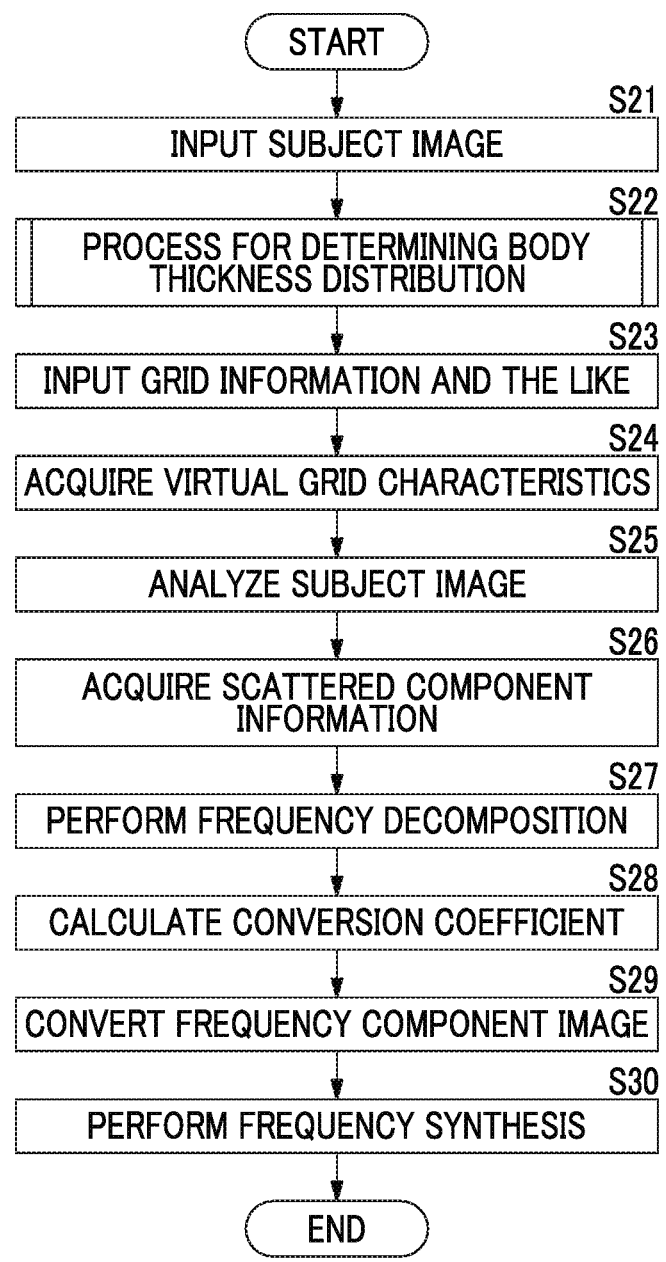
FIG. 6 is a flowchart illustrating a process performed by the radiographic image analysis device according to the third embodiment of the invention.

Next, a third embodiment of the invention will be described with reference to FIGS. 5 and 6. FIG. 5 is a block diagram schematically illustrating the structure of a radiography system to which a radiographic image analysis device according to the third embodiment of the invention is applied. FIG. 6 is a flowchart illustrating a process performed by the radiographic image analysis device according to the third embodiment of the invention.

As illustrated in FIG. 5, the image analysis device 30 according to the third embodiment includes a scattered X-ray analysis unit 43 which performs image processing for a subject image acquired by radiography without using a grid such that the same scattered X-ray removal effect as that of when the subject image is actually captured using the grid is obtained. The scattered X-ray analysis unit 43 includes a characteristic acquisition unit 39 which will be described below, the scattered X-ray information acquisition unit 36, and the scattered X-ray removal unit 37. The image analysis device 30 according to the third embodiment differs from the image analysis device 30 according to each of the above-described embodiments in that it further includes the characteristic acquisition unit 39 that acquires virtual grid characteristics which are the characteristics of a virtual grid, the scattered X-ray information acquisition unit 36 further acquires scattered component information indicating a scattered component of an X-ray included in the subject image Ik as scattered X-ray information, and the scattered X-ray removal unit performs a process of removing scattered X-rays in the subject image acquired by the radiation detector 14, on the basis of the virtual grid characteristics acquired by the characteristic acquisition unit 39 and the scattered component information acquired by the scattered X-ray information acquisition unit 36. The image analysis device 30 according to the third embodiment has the same components as the image analysis device 30 illustrated in FIG. 1 and the functions and processes of each component are substantially the same as those in the above-described embodiments except for the above-mentioned difference. Therefore, the description is focused on the difference from the first embodiment and the description of the same components will not be repeated.

The characteristic acquisition unit 39 acquires the virtual grid characteristics which are input by the operator through the input unit 38. In the third embodiment, the virtual grid characteristics are the scattered X-ray transmissivity Ts of the virtual grid and the transmissivity (primary X-ray transmissivity) Tp of the primary X-rays which pass through the subject K and are directly emitted to the radiation detector 14. The scattered X-ray transmissivity Ts and the primary X-ray transmissivity Tp have a value in the range of 0 to 1.

The characteristic acquisition unit 39 may directly receive the values of the scattered X-ray transmissivity Ts and the primary X-ray transmissivity Tp and acquire the virtual grid characteristics. In the third embodiment, the characteristic acquisition unit 39 receives at least one of grid information indicating the type of grid, information (subject information) about the subject, and imaging conditions when the subject image Ik is acquired, which are designated by the operator, and acquires the virtual grid characteristics, that is, the scattered X-ray transmissivity Ts and the primary X-ray transmissivity Tp. Hereinafter, the imaging conditions used in the characteristic acquisition unit 39 are referred to as imaging conditions for acquiring characteristics.

Here, the grid information includes at least one of information items for specifying the type of grid, such as a grid ratio, grid density, information indicating whether the grid is a convergence type or a parallel type, a focusing distance when the grid is a convergence type, and an interspace material (for example, aluminum, fiber, or Bakelite). The scattered X-ray transmissivity Ts and the primary X-ray transmissivity Tp vary depending on the type of grid. Therefore, for the grid information, a table in which at least one of various kinds of grid information is associated with the virtual grid characteristics is stored in the storage unit 42.

The subject information includes the type of subject such as the chest, the abdomen, and the head. Here, when the subject image Ik is captured, the type of grid used is generally determined according to the part to be captured by radiography, and the scattered X-ray transmissivity Ts and the primary X-ray transmissivity Tp vary depending on the type of grid. Therefore, for the subject information, a table in which various kinds of subject information are associated with the virtual grid characteristics is stored in the storage unit 42.

The imaging conditions for acquiring characteristics include at least one of a source to image-receptor distance (SID) during radiography, a radiography dose, a tube voltage, materials forming the target of the X-ray source and a filter, and the type of radiation detector used for radiography. Here, when the subject image Ik is captured, the type of grid used is generally determined according to the imaging conditions and the scattered X-ray transmissivity Ts and the primary X-ray transmissivity Tp vary depending on the type of grid. Therefore, for the imaging conditions for acquiring characteristics, a table in which various imaging conditions for acquiring characteristics are associated with the virtual grid characteristics is stored in the storage unit 42. The imaging conditions for acquiring characteristics may be the same as imaging conditions used to determine the body thickness distribution (imaging conditions for determining the body thickness distribution) or imaging conditions for acquiring scattered X-ray information which are used to acquire scattered X-ray information, which will be described below, as long as they include parameters required to acquire the virtual grid characteristics, or may be different from these imaging conditions.

The characteristic acquisition unit 39 acquires the virtual grid characteristics with reference to the table stored in the storage unit 42, on the basis of at least one of the grid information, the subject information, and the imaging conditions for acquiring characteristics which are input from the input unit 38. In addition, it is preferable that the grid information, the subject information, and the imaging conditions for acquiring characteristics are directly input through the input unit 38. For example, the following structure may be used: a list of various kinds of grid information, various kinds of subject information, and various imaging conditions for acquiring characteristics is displayed on the display unit 40; and when the operator selects at least one of the grid information, the subject information, and the imaging conditions for acquiring characteristics from the list, the grid information, the subject information, and the imaging conditions for acquiring characteristics are input.

In the third embodiment, the scattered X-ray removal process is performed by performing frequency decomposition for the subject image Ik, which will be described below. In the third embodiment, the virtual grid characteristics are acquired for each of a plurality of frequency bands of the subject image Ik obtained by frequency decomposition. Therefore, the virtual grid characteristics in the above-mentioned table are associated with each of the plurality of frequency bands.

In addition, a table in which all of the grid information, the subject information, and the imaging conditions for acquiring characteristics are associated with the virtual grid characteristics may be stored in the storage unit 42 and the virtual grid characteristics may be acquired on the basis of all of the grid information, the subject information, and the imaging conditions for acquiring characteristics. In this case, the table is at least a four-dimensional table in which various kinds of grid information, various kinds of subject information, various imaging conditions for acquiring characteristics, and virtual grid characteristics are associated with each other.

An exposure factor which is the rate of increase in an irradiation dose which is increased by the use of the grid, a contrast improvement coefficient which is the ratio of contrast when the grid is used and when the grid is not used, and selectivity which is the ratio of primary X-ray transmissivity to scattered X-ray transmissivity are characteristic values indicating the characteristics of the grid. It is possible to calculate the scattered X-ray transmissivity Ts and the primary X-ray transmissivity Tp from these characteristic values. Therefore, the characteristic acquisition unit 39 may receive at least one of the exposure factor, the contrast improvement coefficient, and the selectivity which are designated by the operator and calculate and acquire the virtual grid characteristics, that is, the scattered X-ray transmissivity Ts and the primary X-ray transmissivity Tp.

In the third embodiment, the image analysis device 30 performs the scattered X-ray removal process on the basis of scattered component information, in addition to the virtual grid characteristics. Therefore, the scattered X-ray information acquisition unit 36 further acquires the scattered component information as the scattered X-ray information. In the third embodiment, the scattered component information is a scattered X-ray content distribution of the subject image Ik in which, when the subject K is, for example, the chest, the amount of scattered X-ray is large in a central portion of the subject image Ik in which a mediastinum is present and is small in a peripheral portion in which the lung field is present.

The scattered X-ray information acquisition unit 36 analyzes the subject image Ik acquired by radiography to acquire the scattered component information, that is, the scattered X-ray content distribution. The subject image Ik is analyzed on the basis of irradiation field information, subject information, and imaging conditions when the subject image Ik is captured.

The irradiation field information is information indicating an irradiation field distribution related to the position and magnitude of an irradiation field included in the subject image Ik when radiography is performed using an irradiation field stop. The subject information is information related to, for example, the position of the subject on the subject image Ik, the composition distribution of the subject, the size of the subject, and the thickness of the subject, in addition to the type of subject, such as a chest, abdomen, or head. The imaging conditions used in the scattered X-ray information acquisition unit 36 are information related to, for example, a radiography dose (a tube current×an irradiation time), a tube voltage, a source to image-receptor distance (SID) during radiography, an air gap (the distance from the subject to the radiation detector), and the characteristics of the radiation detector. Hereinafter, the imaging conditions used in the scattered X-ray information acquisition unit 36 are referred to as imaging conditions for acquiring scattered X-ray information. The imaging conditions for acquiring scattered X-ray information may be the same as the imaging conditions used to determine the body thickness distribution or the imaging conditions for acquiring characteristics, as long as they include parameters required to acquire the scattered X-ray information, or may be different from these imaging conditions.

The irradiation field information, the subject information, and the imaging conditions for acquiring scattered X-ray information are factors for determining the distribution of the scattered X-rays included in the subject image Ik. For example, the amount of scattered X-rays depends on the size of the irradiation field. The amount of scattered X-rays increases as the thickness of the subject increases and decreases as a gap between the subject and the radiation detector increases. Therefore, it is possible to accurately acquire the scattered X-ray content distribution using these information items.

The scattered X-ray information acquisition unit 36 calculates a primary X-ray image and a scattered X-ray image from the body thickness distribution Tk(x, y) of the subject K on the basis of the following Expressions (13) and (14) and calculates a scattered X-ray content distribution S(x, y) from the calculated primary X-ray image and scattered X-ray image on the basis of the following Expression (15). Here, the scattered X-ray content distribution S(x, y) has a value in the range of 0 to 1.

$$Ip(x,y) = Io(x,y) \times \exp(-Tk(x,y) \times \mu) \quad (13)$$

$$Is(x,y) = Io(x,y) * S\sigma(Tk(x,y)) \quad (14)$$

$$S(x,y) = Is(x,y)/(Is(x,y) + Ip(x,y)) \quad (15)$$

In the above-mentioned expressions, (x, y) is the coordinates of a pixel position of the subject image Ik, Ip(x, y) is a primary X-ray image at the pixel position (x, y), Is(x, y) is a scattered X-ray image at the pixel position (x, y), Io(x, y) is a radiation dose which is incident on the surface of the subject at the pixel position (x, y), μ is a linear attenuation coefficient of the subject, and Sσ (Tk(x, y)) is a convolution kernel indicating scattering characteristics corresponding to the thickness of the subject at the pixel position (x, y). The above-mentioned Expressions (2) and (13) are based on a known exponential attenuation law and Expression (14) is based on the method disclosed in "J M Boon et al, An analytical model of the scattered radiation distribution in diagnostic radiology, Med. Phys. 15 (5), September/October 1988" (Reference Literature 1). In Expressions (13) and (14), the incident radiation dose Io(x, y) on the surface of the subject is cancelled by division when S(x, y) is calculated even if it is defined as any value. Therefore, the incident dose Io(x, y) may have any value. For example, the incident dose Io(x, y) is 1.

Here, "*" in Expression (14) is an operator indicating a convolution operation. The nature of the kernel varies depending on, for example, an irradiation field distribution, the composition distribution of the subject, an irradiation dose during radiography, a tube voltage, the source to image-receptor distance, an air gap, and the characteristics of the radiation detector, in addition to the thickness of the subject. According to the method described in Reference Literature 1, the scattered X-ray can be approximated by the convolution of the point spread function (Sσ(Tk(x, y) in Expression (14)) with respect to the primary X-ray. In addition, Sσ(Tk(x, y)) can be experimentally calculated on the basis of, for example, the irradiation field information, the subject information, and the imaging conditions for acquiring scattered X-ray information.

In the third embodiment, Sσ(Tk(x, y)) may be calculated on the basis of the irradiation field information, the subject information, and the imaging conditions for acquiring scattered X-ray information during radiography. In addition, a table in which various kinds of irradiation field information, various kinds of subject information, various imaging conditions for acquiring scattered X-ray information, and Sσ(Tk (x, y)) are associated with each other may be stored in the storage unit 42 and Sσ(Tk(x, y)) may be calculated with reference to the table on the basis of the irradiation field information, the subject information, and the imaging conditions for acquiring scattered X-ray information during radiography. Furthermore, Sσ(Tk(x, y)) may be approximated by Tk(x, y).

The scattered X-ray removal unit 37 performs the scattered X-ray removal process of reducing a frequency component in a frequency band that is regarded as the scattered X-ray in the subject image Ik, on the basis of the virtual grid characteristics and the scattered component information. Therefore, the scattered X-ray removal unit 37 performs a process of performing frequency decomposition for the subject image Ik to acquire frequency components in a plurality of frequency bands and reducing the gain of at least one frequency component, combines the processed frequency component with the other frequency components, and acquires the subject image Ik subjected to the scattered X-ray removal process. In addition, any known method, such as wavelet transformation or Fourier transformation, may be used as the frequency decomposition method, in addition to a method that performs multi-resolution conversion for the subject image Ik.

The scattered X-ray removal unit 37 calculates a conversion coefficient R(x, y) for converting a frequency component from the scattered X-ray transmissivity Ts and the primary X-ray transmissivity Tp which are the virtual grid characteristics, and the scattered X-ray content distribution S(x, y), using the following Expression (16).

$$R(x,y) = S(x,y) \times Ts + (1 - S(x,y)) \times Tp \quad (16)$$

Since the scattered X-ray transmissivity Ts, the primary X-ray transmissivity Tp, and the scattered X-ray content distribution S(x, y) have a value in the range of 0 to 1, the conversion coefficient R(x, y) also has a value in the range of 0 to 1. The scattered X-ray removal unit 37 calculates the conversion coefficient R(x, y) for each of a plurality of frequency bands.

In the following description, it is assumed that the pixel value of the subject image Ik is represented by Ik(x, y), a frequency component image obtained by frequency decomposition is represented by Ik(x, y, r), frequency synthesis is represented by Ik(x, y)=ΣrIk(x, y, r), a conversion coefficient for each frequency band is represented by R(x, y, r), and scattered X-ray transmissivity and primary X-ray transmissivity for each frequency band are represented by Ts(r) and Tp(r), respectively. In addition, it is assumed that "r" indicates the layer of the frequency band and the frequency decreases as "r" increases. Therefore, Ik(x, y, r) is a frequency component image in a certain frequency band. It is preferable to use the scattered X-ray content distribution S(x, y) of the subject image Ik without any change. Similarly to the scattered X-ray transmissivity Ts and the primary X-ray transmissivity Tp, the scattered X-ray content distribution S(x, y) may be acquired for each frequency band.

In the third embodiment, the conversion coefficient R(x, y, r) is calculated for each frequency component, the frequency component image Ik(x, y, r) is multiplied by the conversion coefficient R(x, y, r) of a corresponding frequency band to convert the pixel value of the frequency component image Ik(x, y, r), and frequency synthesis is performed for the frequency component image Ik(x, y, r) multiplied by the conversion coefficient R(x, y, r) (that is, Ik(x, y, r)×R(x, y, r)) to acquire a processed subject image Ik'(x, y). Therefore, the process performed by the scattered X-ray removal unit 37 is represented by the following Expression (17). Since the conversion coefficient R(x, y, r) has a value in the range of 0 to 1, the frequency component Ik(x, y, r) is multiplied by the conversion coefficient R(x, y, r) of a corresponding frequency band to reduce the pixel value at the pixel position (x, y), that is, the gain of the frequency component.

$$Ik'(x, y) = \sum r\{Ik(x, y, r) \times R(x, y, r)\} \quad (17)$$
$$= \sum r\{Ik(x, y, r) \times (S(x, y) \times Ts(r) + (1 - S(x, y)) \times Tp(r))\}$$

In the third embodiment, it is assumed that the subject image Ik is decomposed into six frequency bands and the scattered X-ray transmissivity Ts and the primary X-ray transmissivity Tp are acquired for six frequency bands. In this case, the scattered X-ray transmissivity Ts and the primary X-ray transmissivity Tp have values represented by, for example, the following Expression (18). In Expression (18), it is assumed that the value of the frequency band is reduced toward the right side.

$$Ts=\{0.7,0.7,0.7,0.7,0.3,0.2\}$$
$$Tp=\{0.7,0.7,0.7,0.7,0.7,0.7\} \quad (18)$$

As shown in Expression (18), the scattered X-ray transmissivity Ts and the primary X-ray transmissivity Tp have the same value in a high frequency band (r=1 to 4) and the scattered X-ray transmissivity Ts is lower than the primary X-ray transmissivity Tp in a low frequency band (r=5 to 6). The reason is that the removal rate of the grid becomes higher in the lower frequency band in which the frequency component of the scattered X-ray is dominant and the frequency dependence of the removal rate on the primary X-ray is small.

For example, according to a subject image of the chest obtained by radiography, in the range of the mediastinal part and the lung field in which the content of the scattered X-ray is high, the value of the conversion coefficient calculated on the basis of Expressions (16) and (18) is large and the pixel value is largely reduced. Therefore, in the processed subject image Ik' (processed image Ik') acquired by the process represented by Expression (17) using the calculated conversion coefficient, the scattered X-ray component is removed according to the type of grid which is expected to be used.

The scattered X-ray removal unit 37 may remove the scattered X-rays of the subject image Ik as follows. First, similarly to the above, when frequency synthesis is represented by Ik(x, y)=ΣrIk(x, y, r), the scattered X-ray removal unit 37 decomposes the frequency component image Ik(x, y, r) into a scattered X-ray image (scattered X-ray component) Is(x, y, r) and a primary X-ray image (primary X-ray component) Ip(x, y, r) on the basis of the scattered X-ray content distribution S(x, y), using the following Expression (19).

$$Is(x,y,r)=S(x,y)\times Ik(x,y,r)$$
$$Ip(x,y,r)=(1-S(x,y))\times Ik(x,y,r) \quad (19)$$

The scattered X-ray removal unit 37 applies the scattered X-ray transmissivity Ts(r) and the primary X-ray transmissivity Tp(r), which are the virtual grid characteristics, to the scattered X-ray component Is(x, y, r) and the primary X-ray component Ip(x, y, r) to perform image conversion and calculates a converted scattered X-ray component Is'(x, y, r) and a converted primary X-ray component Ip'(x, y, r), using the following Expression (20).

$$Is'(x,y,r)=Is(x,y,r)\times Ts(r)=(x,y)\times Ik(x,y,r)\times Ts(r)$$
$$Ip'(x,y,r)=Ip(x,y,r)\times Tp(r)=(1-S(x,y))\times Ik(x,y,r)\times Tp(r) \quad (20)$$

Then, frequency synthesis is performed for the scattered X-ray component Is'(x, y, r) and the primary X-ray component Ip'(x, y, r) to calculate a processed subject image Ik(x, y)', using the following Expression (21).

$$Ik'(x, y) = \sum r\{Is'(x, y, r) + Ip'(x, y, r)\} \quad (21)$$
$$= \sum r\{S(x, y) \times Ik(x, y, r) \times Ts(r) + (1 - S(x, y)) \times Ik(x, y, r) \times Tp(r)\}$$
$$= \sum r\{Ik(x, y, r) \times (S(x, y) \times Ts(r) + (1 - S(x, y)) \times Tp(r))\}$$

Next, a process performed in the third embodiment will be described. FIG. 6 is a flowchart illustrating the process performed in the third embodiment. When the subject image Ik acquired by the imaging device 10 is input to the image analysis device 30 (S21), a process of determining the body thickness distribution of the subject image Ik is performed, similarly to the first embodiment (S22). S22 corresponds to the process from S02 to S06 illustrated in FIG. 2. Then, the characteristic acquisition unit 39 receives at least one of the grid information, the subject information, and the imaging conditions input from the input unit 38 (for example, the input of the grid information, S23) and acquires the virtual grid characteristic, that is, the scattered X-ray transmissivity Ts and the primary X-ray transmissivity Tp (S24).

The scattered X-ray information acquisition unit 36 analyzes the subject image Ik (S25) and acquires scattered X-ray component information, that is, the scattered X-ray content distribution S(x, y) (S26). The scattered X-ray removal unit 37 performs frequency decomposition for the subject image Ik (S27). The process in S23 and S24, the process in S25 and S26, and the process in S27 may be performed in parallel, the process in S25 and S26 may be performed first, or the process in S27 may be performed first.

Then, the scattered X-ray removal unit 37 calculates the conversion coefficient R(x, y, r) for each frequency band using Expression (16) (S28) and converts the frequency component image Ik(x, y, r) using the conversion coefficient R(x, y, r) (S29). Then, the scattered X-ray removal unit 37 performs frequency synthesis for the converted frequency component image Ik'(x, y, r) to acquire the processed image Ik' (S30) and ends the process. The processed image Ik' is displayed on the display unit 40 and is then used for diagnosis, or it is transmitted to an external image server and is then stored therein.

As such, in the third embodiment, the image analysis device 30 includes the scattered X-ray analysis unit 43 which performs image processing for the subject image acquired by radiography without using the grid such that the same scattered X-ray removal effect as that when the subject image is captured actually using the grid is obtained, acquires the virtual grid characteristics, which are the characteristics of the grid used to remove the scattered X-rays when the subject image Ik is captured, further acquires the scattered X-ray component information, and performs the process of removing the scattered X-rays of the subject image Ik on the basis of the virtual grid characteristics and the scattered X-ray component information. Therefore, the same scattered X-ray removal effect as that obtained by the scattered X-ray removal grid which is actually used can be given to the subject image Ik. In addition, the quality of the subject image Ik can be close to the quality of the subject image which is captured using various types of scattered X-ray removal grids.

When the convergence-type grid is used, there is a concern that concentration unevenness will occur in the subject image Ik due to the oblique incidence of radiation. However, in the third embodiment, since the process of removing the scattered X-rays from the subject image which is captured without using a grid is performed, concentration unevenness due to the oblique incidence of radiation does not occur and it is possible to acquire a high-quality processed image Ik'.

Next, a fourth embodiment of the invention will be described. In the fourth embodiment, an image analysis device has the same structure as the image analysis device according to the third embodiment and only the process performed by the image analysis device is different from that in the third embodiment. Therefore, in this embodiment, the detailed description of the device will not be repeated. In the third embodiment, frequency decomposition is performed for the subject image Ik and frequency synthesis is performed for the converted frequency component image to acquire the processed image Ik'. However, the fourth embodiment differs from the third embodiment in that a frequency component in the frequency band to be removed from the subject image Ik is extracted, the scattered X-ray removal process is performed for the extracted frequency component, and the processed frequency component is added to or subtracted from the subject image Ik to acquire the processed image Ik'.

In the fourth embodiment, the scattered X-ray removal unit 37 performs the following process. First, similarly to the third embodiment, frequency decomposition is performed for the subject image Ik to acquire the frequency component image Ik(x, y, r) and a conversion coefficient R'(x, y, r) for removal is calculated for each frequency band by the following Expression (22).

$$R'(x,y) = S(x,y) \times (1 - Ts(r)) + (1 - S(x,y)) \times 1 - Tp(r)) \quad (22)$$

Then, a removal component $\Delta Ik(x, y, r)$ for each frequency band is calculated by the following Expression (23).

$$\begin{aligned}\Delta Ik(x, y, r) &= Ik(x, y, r) \times R'(x, y, r) \\ &= Ik(x, y, r) \times \{S(x, y) \times (1 - Ts(r)) + (1 - S(x, y)) \times \\ &\quad (1 - Tp(r))\}\end{aligned} \quad (23)$$

Then, frequency synthesis is performed for the removal component $\Delta Ik(x, y, r)$ and a frequency-synthesized removal component $\Sigma r \Delta Ik(x, y, r)$ is subtracted from the subject image Ik(x, y) to acquire a processed subject image Ik'(x, y).

$$\begin{aligned}Ik'(x, y) &= Ik(x, y) - \sum r \Delta Ik(x, y, r) \\ &= Ik(x, y) - \sum r\{Ik(x, y, r) \times \{S(x, y) \times (1 - Ts(r)) + \\ &\quad (1 - S(x, y)) \times (1 - Tp(r))\}\}\end{aligned} \quad (24)$$

Next, the process performed in the fourth embodiment will be described. FIG. 7 is a flowchart illustrating the process performed in the fourth embodiment. Since the process from S31 to S37 is the same as the process from S21 to S27 in the third embodiment, the detailed description thereof will not be repeated in this embodiment.

Subsequently to S37, the scattered X-ray removal unit 37 calculates the conversion coefficient R'(x, y, r) for removal for each frequency band using Expression (22) (S38) and calculates the removal component $\Delta Ik(x, y, r)$ for each frequency band using Expression (23) (S39). Then, the scattered X-ray removal unit 37 performs frequency synthesis for the removal component $\Delta Ik(x, y, r)$ (S40) and subtracts the frequency-synthesized removal component $\Sigma r \Delta Ik(x, y, r)$ from the subject image Ik to acquire the processed image Ik' (S41). Then, the scattered X-ray removal unit 37 ends the process. The processed image Ik' is displayed on the display unit 40 and is then used for diagnosis, or it is transmitted to an external image server and is then stored therein.

In the fourth embodiment, the scattered X-ray removal unit 37 may remove the scattered X-ray of the subject image Ik as follows. First, similarly to the above, when frequency decomposition is represented by Ik(x, y)=$\Sigma r Ik(x, y, r)$, the frequency component image Ik(x, y, r) is decomposed into a scattered X-ray component Is(x, y, r) and a primary X-ray component Ip(x, y, r) by Expression (19), using the scattered X-ray content distribution S(x, y). In addition, the scattered X-ray removal unit 37 respectively applies the scattered X-ray transmissivity Ts(r) and the primary X-ray transmissivity Tp(r), which are the virtual grid characteristics, to the scattered X-ray component Is(x, y, r) and the primary X-ray component Ip(x, y, r) to perform image conversion and calculates a scattered X-ray removed component $\Delta Is(x, y, r)$ and a primary X-ray removed component $\Delta Ip(x, y, r)$, using the following Expression (25).

$$\Delta Is(x,y,r)=Is(x,y)\times(1-Ts(r))=S(x,y)\times Ik(x,y)\times(1-Ts(r))$$

$$\Delta Ip(x,y,r)=Ip(x,y)\times(1-Tp(r))=(1-S(x,y))\times Ik(x,y)\times(1-Tp(r)) \quad (25)$$

Then, the scattered X-ray removal unit 37 performs frequency synthesis for the scattered X-ray removed component ΔIs(x, y, r) and the primary X-ray removed component ΔIp(x, y, r) and subtracts the frequency-synthesized scattered X-ray removed component ΣrΔIs(x, y, r) and primary X-ray removed component ΣrΔIp(x, y, r) from the subject image Ik to calculate a processed subject image Ik'(x, y), using the following Expression (26).

$$Ik'(x,y)=Ik(x,y)-\Sigma r(\Delta Is(x,y,r)+\Delta Ip(x,y,r)) \quad (26)$$

In the third and fourth embodiments, preferably, the subject image Ik has a pixel value that is proportional to an incident dose on the radiation detector, the scattered X-ray removal process is performed for a radiation dose in a linear space, and logarithmic conversion is performed to convert the linear space into a logarithmic linear space that is proportional to human vision.

In the third and fourth embodiments, the characteristic acquisition unit 39 acquires the scattered X-ray transmissivity Ts and the primary X-ray transmissivity Tp as the virtual grid characteristics. However, the characteristic acquisition unit 39 may acquire only one of the scattered X-ray transmissivity Ts and the primary X-ray transmissivity Tp.

In the third and fourth embodiments, the scattered X-ray removal process is performed for the subject image Ik acquired by radiography without using a grid. However, the scattered X-ray removal process may be performed for the subject image Ik acquired by radiography using a grid. In this case, a process of removing a fringe caused by the grid is performed for the subject image and then the scattered X-ray removal process is performed. The scattered X-ray removal process may acquire a radiographic image (first-grid-used image) that is captured using a first grid, which is a desired grid, acquire the virtual grid characteristics corresponding to a desired virtual grid, and convert the amounts of scattered X-rays and primary X-rays in the acquired first-grid-used image into the amounts of scattered X-rays and primary X-rays which correspond to the grid corresponding to the acquired virtual grid characteristics (the grid having the scattered X-ray transmissivity and the primary X-ray transmissivity which are the acquired virtual grid characteristics). In addition, any of the first grid and the grid corresponding to the virtual grid characteristics may have a higher scattered X-ray removal effect and these grids may be arbitrarily selected according to the purpose or circumstances. For example, the method disclosed in JP2012-203504A can be used as the process of removing the fringe caused by the grid.

In addition, the scattered X-ray removal process in the third and fourth embodiments may be performed for a processed image obtained by applying one virtual grid characteristic (first virtual grid characteristic) to the subject image which is captured without using a grid and by performing the scattered X-ray removal process for the subject image. In this case, the first virtual grid characteristic and a first processed image that is a processed image to which the first virtual grid characteristic has been applied may be acquired and a second virtual grid characteristic which corresponds to a desired virtual grid and is different from the first virtual grid characteristic may be acquired. Then, the amounts of scattered X-rays and primary X-rays in the first processed image may be converted into the amounts of scattered X-rays and primary X-rays corresponding to the second virtual grid characteristic on the basis of the second virtual grid characteristic. In addition, any of the first virtual grid characteristic and the second virtual grid characteristic may have a higher scattered X-ray removal effect and these characteristics may be arbitrarily selected according to the purpose or circumstances.

On the basis of the subject image which is captured using a grid with a grid ratio of 3:1 (or the first processed image obtained by performing the scattered X-ray removal process for the subject image captured without using a grid, on the basis of the first virtual grid characteristic), a processed image that seems to be captured using a grid with a grid ratio of 10:1 which is different from the grid used can be virtually acquired by the above-mentioned process. Conversely, on the basis of the subject image which is captured using the grid with a grid ratio of 10:1 (or the first processed image obtained by performing the scattered X-ray removal process for the subject image captured without using a grid, on the basis of the first virtual grid characteristic), a processed image that seems to be captured using the grid with a grid ratio of 3:1 which is different from the grid used can be virtually acquired by the above-mentioned process. In these cases, even when the radiographic image of the subject is repeatedly captured, it is possible to easily acquire a radiographic image with a converted grid ratio. Therefore, the processed image subjected to the scattered X-ray removal process using a grid with a desired grid ratio can be acquired from the subject image which is captured using a grid with an unintended grid ratio or the first processed image. As a result, it is possible to meet the demand for observing the processed image subjected to the scattered X-ray removal process at different levels, without capturing the radiographic image of the subject again.

As a detailed method, for example, in the third embodiment, a table in which Sσ indicating the characteristics of scattering in Expression (14) is associated with each combination of before-conversion grid information corresponding to the grid before conversion and after-conversion grid information corresponding to the grid after conversion is stored in the storage unit 42. In addition, it is assumed that Sσ in the table is experimentally calculated in advance so as to relatively convert the characteristics of scattering caused by the grid before conversion into the characteristics of scattering caused by the grid after conversion. Then, the scattered X-ray information acquisition unit 36 acquires first grid information corresponding to the grid that is actually used (or the virtual grid) as the before-conversion grid information, acquires second grid information corresponding to the desired virtual grid as the after-conversion grid information, and acquires Sσ corresponding to the first grid information and the second grid information on the basis of the table. Then, the scattered X-ray information acquisition unit 36 sets Io(x, y) to, for example, 1 and calculates the primary X-ray image Ip(x, y) and the scattered X-ray image Is(x, y) on the basis of the acquired Sσ, using Expression (13) and Expression (14). Then, the scattered X-ray information acquisition unit 36 may calculate the scattered X-ray content distribution S(x, y) on the basis of the calculated primary X-ray image Ip(x, y) and scattered X-ray image Is(x, y), using Expression (15).

In addition, the scattered X-ray removal unit 37 may perform the scattered X-ray removal process as follows. The scattered X-ray removal unit 37 acquires the first grid characteristic (primary X-ray transmissivity Tp1 and scattered X-ray transmissivity Ts1) corresponding to the grid (or the virtual grid) which is actually used and the second virtual grid characteristic (primary X-ray transmissivity Tp2 and scattered X-ray transmissivity Ts2) corresponding to a desired virtual grid, for the scattered X-ray transmissivity Ts and the primary X-ray transmissivity Tp for each frequency band represented by Expression (18). In addition, the scattered X-ray removal unit 37 acquires Tp2/Tp1 as the primary X-ray transmissivity Tp represented by Expression (18) and Ts2/Ts1 as the scattered X-ray transmissivity Ts represented by Expression (18), in order to relatively convert the characteristics of scattering due to the first grid before conversion into the characteristics of scattering due to the second grid after conversion. Then, the scattered X-ray removal unit 37 applies the acquired scattered X-ray transmissivity Ts (=Ts2/Ts1) and primary X-ray transmissivity Tp (=Tp2/Tp1) to Expression (16) to calculate the conversion coefficient R and performs the scattered X-ray removal process using the conversion coefficient R, similarly to the third embodiment. In Expression (16), in some cases, the conversion coefficient R(x, y) has a value greater than 1 when the scattered X-ray transmissivity Ts2, which is the second grid characteristic, is higher than the scattered X-ray transmissivity Ts1, which is the first grid characteristic.

The first grid characteristic and the second grid characteristic may be acquired by any method. For example, a table in which the grid characteristics (the primary X-ray transmissivity Tp and the scattered X-ray transmissivity Ts) that are experimentally calculated in advance are associated with each grid information item may be prepared and stored in the storage unit 42. Then, the scattered X-ray removal unit 37 may acquire the first and second grid information items and acquire the first and second grid characteristics corresponding to the first and second grid information items on the basis of the table. In addition, the first and second grid characteristics may be acquired on the basis of the user's input from the input unit 38. The grid information may be acquired by an input from the input unit 38. For example, as described in JP2003-260053A, protrusions corresponding to the type of grid may be formed on the grid and then detected to acquire the grid information.

There is a demand for image observation using the subject image which has been captured without using a scattered X-ray removal grid, depending on the part to be subjected to radiography. It is not preferable to perform the scattered X-ray removal process according to the third and fourth embodiments for the subject image obtained by capturing the radiographic image of the part. Therefore, it is preferable to switch the turn-on and turn-off of the scattered X-ray removal process according to the third embodiment, according to the part to be subjected to radiography. Information about the part to be subjected to radiography may be input from the operator or may be automatically acquired from a radiography request input from a known console PC (not illustrated) which controls the flow of radiography, or the system may use information which is stored so as to be associated with the subject image as the information about the part to be subjected to radiography after radiography. When it is difficult to acquire the information, a part recognition process may be performed for the subject image to acquire the information. In this case, a table in which the turn-on and turn-off of the process are associated with each part may be stored in the storage unit 42 and the process may be turned on or off with reference to the table.

In the third and fourth embodiments, both the processed image Ik' and the subject image Ik before processing may be displayed and any one of the subject image Ik to be used for diagnosis may be selected.

In some cases, the previous subject image is used to perform comparative observation over time in order to checks the state of progress or treatment of disease. In this case, when the subject image (referred to as a first subject image) which is captured without using the scattered X-ray removal grid is compared with the subject image (referred to as a second subject image) which is captured using the scattered X-ray removal grid, it is preferable to correct the conditions of the scattered X-ray removal process according to the third or fourth embodiment, on the basis of processing conditions when a process of removing fringes caused by the grid is performed for the first subject image, such that the qualities of the first and second subject images are equal to each other.

A series of processes (S22 in FIG. 6 and S32 in FIG. 7) for determining the body thickness distribution of the subject image Ik in the third and fourth embodiments may be any process (a body thickness distribution determination process according to the invention) for determining the body thickness distribution Tk of the subject K as long as it includes at least the following processes: the process of the virtual model acquisition unit 32 acquiring a virtual model of the subject having a predetermined body thickness distribution; the process of the estimated image generation unit 33 generating a composite image of the estimated primary X-ray image, which is obtained by estimating the primary X-ray image of the virtual model obtained by radiography from the virtual model, and the estimated scattered X-ray image, which is obtained by estimating the scattered X-ray image of the virtual model obtained by radiography from the virtual model, as an estimated image which is obtained by estimating the subject image of the subject obtained by radiography; the process of the correction unit 34 correcting the body thickness distribution of the virtual model such that the difference between the estimated image and the subject image is reduced; and the process of the body thickness distribution determination unit 35 determining the corrected body thickness distribution of the virtual model as the body thickness distribution of the subject. For example, a series of processes (S22 in FIG. 6 and S32 in FIG. 7) for determining the body thickness distribution may include the processes corresponding to the second embodiment. In addition, a series of processes (S22 in FIG. 6 and S32 in FIG. 7) for determining the body thickness distribution of the subject image Ik in the third and fourth embodiments may be performed at any time as long as it is performed before the process of the scattered X-ray information acquisition unit 36 calculating the primary X-ray image and the scattered X-ray image from the body thickness distribution Tk(x, y) of the subject K, on the basis of Expressions (13) and (14).

In a case in which a series of processes (see S02 to S06 in FIG. 2) for determining the body thickness distribution of the subject image according to the invention is performed after the subject image Ik is acquired, other desired image processing, such as the scattered X-ray removal process, is performed to generate a processed image using the determined body thickness distribution of the subject image, and the processed image is displayed, it is preferable to minimize the time required from the acquisition of the subject image to the display of the processed image (the time from the acquisition of the subject image to the display of the processed image obtained by the process of determining the body thickness distribution of the subject image and other desired image processing such as the scattered X-ray removal process for the subject image). For this purpose, in a series of processes for determining the body thickness distribution of the subject image in each of the above-described embodiments, the image acquisition unit 31 may reduce the subject image to a predetermined size to generate a reduced image and acquire the reduced image, the virtual model acquisition unit 32 may acquire a virtual model with a size corresponding to the reduced image, the estimated image generation unit 33 may generate an estimated image with a size corresponding to the reduced image, the correction unit 34 may correct the body thickness distribution of the virtual model such that the difference between the estimated image and the reduced image is reduced, and the body thickness distribution determination unit 35 may determine the corrected body thickness distribution of the virtual model as the body thickness distribution of the subject which is enlarged to a desired size such as the size of the subject image Ik. In this case, the processing load of at least one process (particularly, for example, the process of the estimated image generation unit 33 generating the estimated image with a size corresponding to the reduced image and the process of the correction unit 34 correcting the body thickness distribution of the virtual model such that the difference between the estimated image and the reduced image is reduced) included in the processes for determining the body thickness distribution of the subject image is likely to be reduced. In addition, the time from the acquisition of the subject image to the display of the processed image is reduced and the waiting time of the user is reduced. Therefore, it is possible to assist the efficient observation operation of the user. In addition, the above-mentioned effect is very large and it is possible to significantly reduce the operation time of the user in a situation in which, in medical facilities, a plurality of subject images of a plurality of subjects obtained by radiography are acquired, desired image processing, such as the process of determining the body thickness distribution of the subject image and the scattered X-ray removal process according to each of the above-described embodiments, is sequentially performed for each of the plurality of subject images, and the obtained processed images are sequentially displayed such that the user observes the processed images. In addition, it is preferable to minimize the resolution of the reduced image in the range in which a resolution capable of appropriately determining similarity using characteristic information acquired from the reduced image and the characteristic information of the model image is maintained. Specifically, a compression ratio may be changed in the range in which a characteristic and representative organ or tissue can be identified and a model can be selected for each part of which an image will be captured.

For example, in the case in which, in medical facilities, a plurality of subject images of a plurality of subjects obtained by radiography are acquired, desired image processing, such as the process (for example, see S02 to S06 in FIG. 2) of determining the body thickness distribution of the subject image and the scattered X-ray removal process according to the invention, is sequentially performed for each of the plurality of subject images, and the obtained processed images are sequentially displayed such that the user observes the processed images, it is preferable to effectively use the time from the acquisition of the subject image to the display of the processed image. For example, it is considered that reference information for image observation is displayed before the display of the processed image for the time from the acquisition of the subject image to the display of the processed image according to each of the above-described embodiments.

For example, as a fifth embodiment which is a modification of the image analysis device according to the first embodiment, after a subject image is acquired, for the period for which a series of processes (S02 to S06 in FIG. 2) for determining the body thickness distribution Tk of the subject image Ik is performed, some or all of the following processes may be performed: the scattered X-ray information acquisition unit 36 acquires the scattered X-ray information of the subject image using a predetermined temporary body thickness distribution; and the scattered X-ray removal unit 37 performs the scattered X-ray removal process for the subject image Ik, on the basis of the scattered X-ray information acquired using the temporary body thickness distribution, to generate a temporary processed image, and displays the temporary processed image on the display unit 40 (temporary processed image generation and display process).

FIG. 8 is a flowchart illustrating the fifth embodiment. An image analysis device according to the fifth embodiment differs from the image analysis device according to the first embodiment in that, for the period for which a series of processes (S02 to S06 in FIG. 2) for determining the body thickness distribution Tk of the subject image Ik is performed, the scattered X-ray information acquisition unit 36 acquires scattered X-ray information indicating scattered X-rays included in the subject image k on the basis of a predetermined temporary body thickness distribution and the scattered X-ray removal unit 37 performs the scattered X-ray removal process for the subject image, on the basis of the scattered X-ray information acquired using the temporary body thickness distribution, to generate a temporary processed image and displays the temporary processed image on the display unit 40. For the other portions, the image analysis device according to the fifth embodiment includes the same components as the image analysis device 30 illustrated in FIG. 1 and the functions and processes of each component are substantially the same as those in the first embodiment. Therefore, the description is focused on the difference from the first embodiment and the description of the same portions will not be repeated.

In the fifth embodiment, as illustrated in FIG. 8, the image acquisition unit 31 acquires the subject image Ik, similarly to S01 in the first embodiment (S51), performs a process (S52) of determining the body thickness distribution Tk of the subject image Ik, similarly to the first embodiment (S02 to S06 in FIG. 2), acquires the scattered X-ray information (the primary X-ray image Ip and the scattered X-ray image Is), using the determined body thickness distribution Tk, on the basis of Conditional Expressions (1) and (2), similarly to the optional example of the first embodiment, and subtracts the acquired scattered X-ray image Is from the subject image Ik to perform the scattered X-ray removal process (S53), similarly to the optional example of the first embodiment.

In the fifth embodiment, when the image acquisition unit 31 acquires the subject image (S51), the scattered X-ray information acquisition unit 36 acquires a predetermined temporary body thickness distribution in parallel to the process in S52, acquires the scattered X-ray information (the primary X-ray image Ip and the scattered X-ray image Is), using the acquired temporary body thickness distribution, on the basis of Conditional Expressions (1) and (2), similarly to the optional example of the first embodiment (S55), subtracts a scattered X-ray image Is' which is acquired using the temporary body thickness distribution from the subject image Ik, on the basis of the scattered X-ray image Is', to generate a temporary processed image from which the influence of the scattered X-rays has been removed, similarly to the optional example of the first embodiment, and stores the temporary processed image in the storage unit 42

(S56). Then, the image analysis device 30 determines whether the processed image obtained by the scattered X-ray removal process in S53 has been generated. When the processed image has not been generated (S57, No), the image analysis device 30 displays the temporary processed image on the display unit 40 until the processed image is generated (S58). On the other hand, when the processed image obtained by the process in S53 has been generated (S57, Yes), the image analysis device displays the processed image on the display unit 40 (S54).

According to the fifth embodiment, in a radiographic image analysis device which acquires the subject image Ik, performs a process of determining the body thickness distribution Tk of the subject image Ik, performs desired image processing, such as the scattered X-ray removal process, and displays the obtained processed image, for the period for which a series of processes for determining the body thickness distribution Tk of the subject image Ik is performed, some or all of the following processes are performed: desired image processing, such as a process of removing the scattered X-rays of the subject image, is performed using the predetermined temporary body thickness distribution; the processed image which is obtained using the temporary body thickness distribution is generated as the temporary processed image; and the temporary processed image is displayed on the display unit 40. Therefore, the user can effectively use the time until the processed image is displayed and observe the temporary processed image obtained using the temporary body thickness distribution to roughly check the region of interest in the subject image or whether the radiographic conditions applied to the subject image are correct. Therefore, the user can effectively perform observation and it is possible to provide reference information for the user's observation.

In the fifth embodiment, the "predetermined body thickness distribution" may be any body thickness distribution which substantially corresponds to the subject K. For example, among the body thickness distributions which are obtained from a plurality of previous subject images by a body thickness determination process, the latest body thickness distribution can be used. In addition, the body thickness distribution of a standard subject may be used.

In addition, a series of processes (S52) for determining the body thickness distribution of the subject image Ik in the fifth embodiment may be any process (a body thickness distribution determination process according to the invention) for determining the body thickness distribution Tk of the subject K as long as it includes at least the following processes: the process of the virtual model acquisition unit 32 acquiring a virtual model of the subject having a predetermined body thickness distribution; the process of the estimated image generation unit 33 generating a composite image of the estimated primary X-ray image, which is obtained by estimating the primary X-ray image of the virtual model obtained by radiography from the virtual model, and the estimated scattered X-ray image, which is obtained by estimating the scattered X-ray image of the virtual model obtained by radiography from the virtual model, as an estimated image which is obtained by estimating the subject image of the subject obtained by radiography; the process of the correction unit 34 correcting the body thickness distribution of the virtual model such that the difference between the estimated image and the subject image is reduced; and the process of the body thickness distribution determination unit 35 determining the corrected body thickness distribution of the virtual model as the body thickness distribution of the subject. For example, a series of processes (S52) for determining the body thickness distribution may include the processes corresponding to the second embodiment.

In the fifth embodiment, the process (S53 and S56) of removing the scattered X-rays from the subject image Ik is the same as the process of removing the scattered X-rays from the subject image Ik in the first embodiment. However, any method which can remove the scattered X-rays from the subject image Ik can be applied. For example, in the fifth embodiment, the process (S53 and S56) of removing the scattered X-rays from the subject image Ik may correspond to S23 to S30 in the third embodiment illustrated in FIG. 6 or may correspond to S33 to S41 in the fourth embodiment illustrated in FIG. 7. In the fifth embodiment, the process (S53 and S54) of removing the scattered X-rays from the subject image Ik has been described. However, the invention is not limited thereto. Image processing other than the scattered X-ray removal process may be performed for the subject image Ik, or the scattered X-ray removal process and other types of image processing may be performed for the subject image Ik. The process from S55 to S58 can be performed for any period which partially or entirely overlaps the period of the process in S52 and it is preferable to early perform the process from S55 to S58 after the subject image Ik is acquired, in order to rapidly display the temporary processed image and to rapidly provide reference information for the user's observation.

Figure 2:
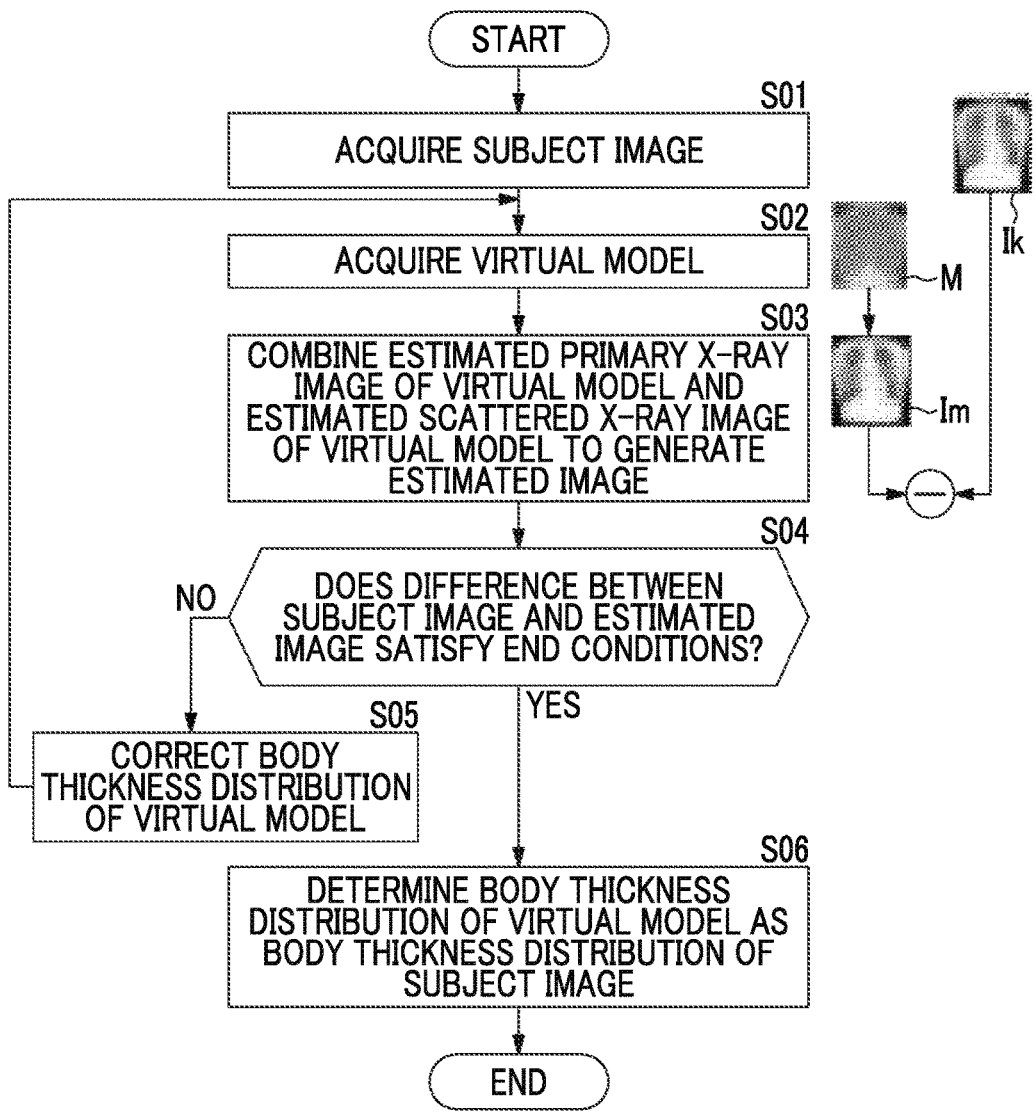
FIG. 2 is a flowchart illustrating a process performed by the radiographic image analysis device according to the first embodiment of the invention.

In each of the above-described embodiments, the process of acquiring the subject image Ik in S01 illustrated in FIG. 2 may be performed at any time as long as it is performed before the process of determining the difference between the subject image and the estimated image in S04.

In the above-described embodiments, the image analysis device 30 may not include the scattered X-ray information acquisition unit 36 and the scattered X-ray removal unit 37 and may not perform the scattered X-ray information acquisition process and the scattered X-ray removal process. In this case, it is considered that the image analysis device 30 outputs the determined body thickness distribution Tk of the subject to another device and the device performs image processing for the subject image Ik or a imaging condition determination process, using the body thickness distribution Tk.

The invention is not limited to the above-described embodiments and the body thickness distribution of the subject obtained by the invention can be used in any process for determining image processing conditions corresponding to the body thickness of the subject for the subject image. For example, it is considered that the body thickness distribution obtained by the invention is used in, for example, a gradation process of adjusting concentration or contrast, a noise removal process, a dynamic range adjustment process, and a frequency emphasis process for the subject image which is a still image or a moving image. In addition, the body thickness distribution obtained by the invention can be used in any process for determining imaging conditions corresponding to the body thickness for the subject image. When the body thickness distribution obtained by the invention is used to determine each image processing condition or imaging conditions, an accurate body thickness distribution is applied to the subject image and it is possible to increase the effect of improving image quality using the determined image processing conditions or imaging conditions.

For example, in an energy subtraction technique which acquires a radiographic image using the difference between two radiographic images acquired by capturing high-energy and low-energy radiations while changing the tube voltage, a process may be performed which determines a weight coefficient such that a large weight is given to a high-energy image at the position where the body thickness is large when a low-energy image is subtracted from the high-energy image according to the body thickness distribution of the subject obtained by the invention. In this case, since an accurate body thickness distribution is applied to the subject image, it is possible to reduce the influence of a beam hardening phenomenon in which the quality of radiation varies depending on the thickness of the subject and to appropriately improve the quality of the processed image.

In the field of a radiolucent image application technique or a technique for capturing the image of the same subject a plurality of times to acquire a plurality of radiographic images, such as a tomosynthesis technique, it is preferable that the body thickness distribution of the subject is acquired from the first subject image by the method according to the invention and the imaging conditions of the subject whose image is to be captured are determined on the basis of the acquired body thickness distribution. The subsequent subject image can be captured under appropriate imaging conditions corresponding to the body thickness. Therefore, it is possible to improve the quality of the subsequent subject image so as to be suitable for diagnosis.

It is preferable to store dose management information in which the body thickness distribution of the subject obtained by the invention is associated with the imaging conditions for each subject. The imaging conditions may include a set value which is set in, for example, the X-ray source or exposure time or may include a measured value, such as a dose that is actually radiated, which is measured by, for example, a detector and exposure time. A plurality of dose management information items about the subject are acquired as dose history information for each subject and the cumulative exposure of the subject at each position for a predetermined period of time is calculated on the basis of the dose history information. In this way, it is possible to provide useful information which is a dose management index for each region indicating whether the cumulative exposure is equal to or greater than a predetermined threshold value beyond an allowable range in a predetermined region such as a predetermined organ. In addition, dose management information about each of a plurality of different subjects can be acquired and statistical analysis can be performed to specify which of the imaging conditions is used according to the tendency of the body thickness distribution. It is possible to provide reference information for determining the imaging conditions of a new subject or for estimating the imaging conditions of the previous subject.

When two subject images forming a stereoscopic image are selected from a plurality of subject images captured by a tomosynthesis device, preferably, the body thickness distribution of the subject obtained by the invention is acquired and two subject images are selected such that an appropriate amount of parallax or an appropriate convergence angle (an angle formed between the imaging directions of two subject images forming the stereoscopic image) is obtained according to the acquired body thickness distribution. For example, the following process can be performed: an index value indicating the characteristics of the body thickness distribution, such as a maximum value, a mean, or a median, is extracted from the body thickness distribution of the subject; parallax determination information which is associated with an appropriate amount of parallax (or an appropriate convergence angle) such that the amount of parallax (or the convergence angle) increases as the body thickness of the subject increases is created for each range of the index value and then acquired; the amount of parallax (or the convergence angle) corresponding to the index value extracted from the body thickness distribution of the subject is determined as the amount of parallax (or the convergence angle) of the stereoscopic image, on the basis of the parallax determination information; and two subject images having the amount of parallax (or the convergence angle) therebetween are selected as the subject images forming the stereoscopic image. For example, the following process can be performed: an index value indicating the characteristics of the body thickness distribution is calculated according to the body thickness distribution of the subject; the subjects are classified into a plurality of body types, such as a thin body type, a standard body type, and a thick body type, by the index value; the amount of parallax (or the convergence angle) corresponding to the divided classification is determined as the amount of parallax of the stereoscopic image of the subject; and two subject images having the amount of parallax therebetween are selected as the subject images forming the stereoscopic image. As such, when two subject images forming the stereoscopic image are selected from a plurality of subject images, the body thickness distribution of the subject obtained by the invention is acquired and two subject images are appropriately selected according to the acquired body thickness distribution such that the amount of parallax or the convergence angle increases as the body thickness increases. In this case, it is possible generate a stereoscopic image with a quality suitable for observation according to the body thickness distribution. For the amount of parallax and the convergence angle, it is possible to refer to the previous patent applications filed by the inventors (for example, JP2013-198736A, JP2013-198508A, and JP2013-154165A).

When the subject image is captured using the convergence-type grid, there is a concern that concentration unevenness occurs due to the oblique incidence of radiation. In order to prevent the occurrence of the concentration unevenness, the following process may be performed: the body thickness distribution obtained by the invention is acquired; when it is known that the subject in the subject image has a bilaterally symmetric body thickness distribution as in a front image of the human body, it is determined whether or not the body thickness distribution is substantially bilaterally symmetric; and when the body thickness distribution is not bilaterally symmetric, an image or a sound indicating that the body thickness distribution is not bilaterally symmetric is displayed or output to prompt the operator to re-capture the subject image. Therefore, it is possible to prevent the generation of a processed image with a quality that is not suitable for observation due to concentration unevenness caused by the oblique incidence of radiation.

Each of the above-described embodiments is illustrative and all of the descriptions should not be used to interpret the technical scope of the invention in a limited manner. The aspects of the invention are not limited to each of the above-described embodiments (the first to fifth embodiments, other modification examples, and application examples) and the invention includes any combination of the components according to each embodiment and various modifications which can be made by those skilled in the art. That is, various additions, changes, and partial deletions can be made, without departing from the conceptual idea and meaning of the invention which are derived from content defined in the claims and equivalents thereof.

In addition, for example, the system configuration, the hardware configuration, the process flow, the module configuration, the user interface, and the specific content of processing can be modified in various ways without departing from the scope and spirit of the invention and these modifications are also included in the technical scope of the invention. For example, some or all of the components of the image analysis device may be implemented by a single workstation or may be implemented by one or more workstations, servers, and the storage devices which are connected to each other through a network.

In the above-described embodiments, the scattered X-ray removal process is performed using the radiographic image acquired by the imaging device 10 which captures the radiographic image of the subject using the radiation detector 14. However, the invention can be applied to the structures disclosed in JP1996-266529A (JP-H08-266529A) and JP1997-24039A (JP-H09-24039A) in which the radiographic image information of the subject is stored and recorded on a storage phosphor sheet as a radiation detector and the radiographic image is photoelectrically read from the storage phosphor sheet and is then used.

What is claimed is:

1. A radiographic image analysis device that analyzes a subject image of a subject obtained by radiography to estimate a body thickness distribution of the subject, the device comprising:
   a memory storing computer executable instructions; and
   a processor configured to execute the stored instructions, which when executed by the processor cause the processor to perform the following operations:
      acquire the subject image;
      acquire a virtual model of the subject having a predetermined body thickness distribution;
      generate a composite image by combining an estimated primary X-ray image and an estimated scattered X-ray image, wherein the estimated primary X-ray image is obtained by X-ray radiography of the virtual model, wherein the estimated scattered X-ray image is obtained based on the X-ray radiography of the virtual model, and wherein the generated composite image serves as an estimate of the X-ray radiographic image of the subject;
      correct the body thickness distribution of the virtual model such that a difference between the estimated image and the subject image is reduced;
      determine the corrected body thickness distribution of the virtual model as the body thickness distribution of the subject;
      acquire scattered X-ray information which is obtained by estimating a scattered X-ray of the subject image, using the determined body thickness distribution of the subject;
      acquire a first virtual grid characteristic which is a characteristic of a virtual scattered X-ray removal grid; and
      perform a process of removing the scattered X-ray of the subject image on the basis of the scattered X-ray information and the first virtual grid characteristic that have been acquired.

2. The radiographic image analysis device according to claim 1,
   wherein the processor further performs the following operations:
      acquire the virtual model having the corrected body thickness distribution,
      generate the estimated image from the virtual model having the corrected body thickness distribution, and
      correct the body thickness distribution of the virtual model such that a difference between the generated estimated image and the subject image is reduced.

3. The radiographic image analysis device according to claim 1,
   wherein the processor is further configured to:
      change the body thickness distribution of the virtual model for each partial region including one or more pixels in the virtual model,
      calculate a body thickness of the partial region at which the difference between the estimated image and the subject image is reduced, and
      correct the body thickness distribution of the virtual model using the calculated body thickness of each partial region.

4. The radiographic image analysis device according to claim 1,
   wherein the predetermined body thickness distribution is created by acquiring a comparative subject image of a comparative subject different from the subject, which is obtained by radiography, and a three-dimensional image of the comparative subject obtained by three-dimensional imaging, and measuring a body thickness of the comparative subject on a straight line corresponding to a radiation path of the comparative subject image at each position of the acquired three-dimensional image.

5. The radiographic image analysis device according to claim 1,
   wherein the virtual model further includes characteristic information indicating at least one of structures included in the virtual model, the arrangement of the structures, and characteristics of the structures with respect to radiation, and
   the processor is further configured to select a parameter for calculating the estimated image according to the structure corresponding to each position of the virtual model, based on the characteristic information, and generate the estimated image.

6. The radiographic image analysis device according to claim 1,
   wherein, in the process of removing the scattered X-ray, the processor is further configured to perform frequency decomposition for the subject image to acquire a frequency component in each of a plurality of frequency bands, perform processing that reduces a gain of the frequency component corresponding to a scattered X-ray component, and synthesize the frequency component for which the processing has been completed and frequency components other than the frequency component.

7. The radiographic image analysis device according to claim 1,
   wherein, in the process of removing the scattered X-ray, the processor is further configured to perform frequency decomposition for the subject image to acquire a frequency component in each of a plurality of frequency bands, extract a removal component which is the frequency component corresponding to a scattered X-ray component, perform frequency synthesis for the extracted removal component, and add the frequency-synthesized removal component to the subject image or subtract the frequency-synthesized removal component from the subject image.

8. The radiographic image analysis device according to claim 1,
wherein the subject image is captured without using a scattered X-ray removal grid.

9. The radiographic image analysis device according to claim 8,
wherein the processor is further configured to acquire a second virtual grid characteristic which is a characteristic of the virtual scattered X-ray removal grid that is different from the first virtual grid characteristic, and
the processor is further configured to acquire a first scattered X-ray removed image, for which the process of removing the scattered X-ray of the subject image based on the scattered X-ray information and the first virtual grid characteristic has been performed, and acquire a second scattered X-ray removed image by converting a scattered X-ray amount and a primary X-ray amount of the first scattered X-ray removed image so as to become a scattered X-ray amount and a primary X-ray amount corresponding to the second virtual grid characteristic.

10. The radiographic image analysis device according to claim 9,
wherein the processor is further configured to acquire information of the first virtual grid as first grid information, and acquire information of the second virtual grid as second grid information, and
the processor is further configured to refer to a table in which a convolution kernel indicating a scattering characteristic relatively converting a characteristic of scattering of the first virtual grid to a characteristic of scattering of the second virtual grid is associated with each combination of the first grid information and the second grid information, and to calculate a scattered X-ray content distribution of the subject image using the convolution kernel corresponding to the combination of the first grid information and the second grid information that have been acquired.

11. The radiographic image analysis device according to claim 9, wherein the processor is further configured to acquire a scattered X-ray transmissivity and a primary X-ray transmissivity of the first virtual grid as the first virtual grid characteristic, to acquire a scattered X-ray transmissivity and a primary X-ray transmissivity of the second virtual grid as the second virtual grid characteristic, and to calculate a conversion coefficient relatively converting the characteristic of scattering of the first virtual grid to the characteristic of scattering of the second virtual grid based on the first grid characteristic and the second grid characteristic.

12. The radiographic image analysis device according to claim 11,
wherein the processor is further configured to acquire information of the first virtual grid as first grid information, and to acquire information of the second virtual grid as second grid information, and
the processor is further configured to refer to a table in which grid information and a grid characteristic corresponding to the grid information are associated with each other in advance, and to acquire the first virtual grid characteristic and the second virtual grid characteristic according to the acquired first and second grid information, respectively.

13. The radiographic image analysis device according to claim 1, wherein the subject image is an image radiographically captured using a scattered X-ray removal grid, and the processor is configured to perform a process of removing a fringe caused by the employed scattered X-ray removal grid used in the radiographic capturing of the subject image from the subject image and perform the process of removing the scattered X-ray of the subject image on which the process of removing the fringe has been performed, based on the scattered X-ray information and the first virtual grid characteristic, to acquire a first scattered X-ray removed image.

14. The radiographic image analysis device according to claim 13, wherein the processor is further configured to acquire the first scattered X-ray removed image by converting the image on which the process of removing the fringe has been performed, such that a scattered X-ray amount and a primary X-ray amount of the image on which the process of removing the fringe has been performed become a scattered X-ray amount and a primary X-ray amount corresponding to the first virtual grid characteristic.

15. The radiographic image analysis device according to claim 14,
wherein the processor is further configured to acquire information of a first grid, which is the employed scattered X-ray removal grid, as first grid information, and to acquire information of a second grid, which is a virtual grid, as second grid information corresponding to the second virtual grid characteristic, and
the processor is further configured to refer to a table in which a convolution kernel indicating a scattering characteristic relatively converting a characteristic of scattering of the first grid to a characteristic of scattering of the second grid is associated with each combination of the first grid information and the second grid information, and to calculate a scattered X-ray content distribution of the subject image using the convolution kernel corresponding to the combination of the first grid information and the second grid information that have been acquired.

16. The radiographic image analysis device according to claim 14, wherein the processor is further configured to acquire a first grid characteristic indicating a scattered X-ray transmissivity and a primary X-ray transmissivity of a first grid, which is the employed scattered X-ray removal grid, and a second virtual grid characteristic indicating a scattered X-ray transmissivity and a primary X-ray transmissivity of a desired virtual grid, and to calculate a conversion coefficient relatively converting a characteristic of scattering of the first grid to a characteristic of scattering of the second grid based on the first grid characteristic and the second grid characteristic.

17. The radiographic image analysis device according to claim 16,
wherein the processor is further configured to acquire information of the first grid, which is the employed scattered X-ray removal grid, as first grid information, and to acquire information of the second grid, which is the virtual scattered X-ray removal grid, as second grid information, and
the processor is further configured to refer to a table in which grid information and a grid characteristic corresponding to the grid information are associated with each other in advance, and to acquire the first virtual grid characteristic and the second virtual grid characteristic according to the acquired first and second grid information, respectively.

18. The radiographic image analysis device according to claim 1, wherein the processor is further configured to acquire a plurality of comparative subject images obtained by radiographically capturing comparative subjects that are different from the subject, measure the comparative subjects to acquire a body thickness distribution of each of the comparative subjects, associate the body thickness distribution of the comparative subject and first body type information indicating a body type of the comparative subject with each other for each of the comparative subjects, acquire second body type information indicating a body type of the subject, specify the body thickness distribution of the comparative subject having the first body type information that is similar to the second body type information, and designate the specified body thickness distribution of the comparative subject as the predetermined body thickness distribution.

19. A radiographic image analysis method that is performed in a radiographic image analysis device and analyzes a subject image which is obtained by irradiating a subject with radiation to estimate a body thickness distribution of the subject, the method comprising:

acquiring the subject image;

acquiring a virtual model of the subject having a predetermined body thickness distribution;

generating a composite image by combining an estimated primary X-ray image and an estimated scattered X-ray image, wherein the estimated primary X-ray image is obtained by X-ray radiography of the virtual model, wherein the estimated scattered X-ray image is obtained based on the X-ray radiography of the virtual model, and wherein the generated composite image serves as an estimate of the X-ray radiography image of the subject;

correcting the body thickness distribution of the virtual model such that a difference between the estimated image and the subject image is reduced;

determining the corrected body thickness distribution of the virtual model as the body thickness distribution of the subject;

acquiring scattered X-ray information which is obtained by estimating a scattered X-ray of the subject image, using the determined body thickness distribution of the subject;

acquiring a first virtual grid characteristic which is a characteristic of a virtual scattered X-ray removal grid; and performing a process of removing the scattered X-ray of the subject image based on the scattered X-ray information and the first virtual grid characteristic that have been acquired.

20. A non-transitory computer-readable storage medium having stored therein a radiographic image analysis program that analyzes a subject image which is obtained by irradiating a subject with radiation to estimate a body thickness distribution of the subject, the program causing a computer to perform:

acquiring the subject image;

acquiring a virtual model of the subject having a predetermined body thickness distribution;

generating a composite image by combining an estimated primary X-ray image and an estimated scattered X-ray image, wherein the estimated primary X-ray image is obtained by X-ray radiography of the virtual model, wherein the estimated scattered X-ray image is obtained based on the X-ray radiography of the virtual model, and wherein the generated composite image serves as an estimate of the X-ray radiographic image of the subject;

correcting the body thickness distribution of the virtual model such that a difference between the estimated image and the subject image is reduced;

determining the corrected body thickness distribution of the virtual model as the body thickness distribution of the subject;

acquiring scattered X-ray information which is obtained by estimating a scattered X-ray of the subject image, using the determined body thickness distribution of the subject;

acquiring a first virtual grid characteristic which is a characteristic of a virtual scattered X-ray removal grid; and performing a process of removing the scattered X-ray of the subject image on the basis of the scattered X-ray information and the first virtual grid characteristic that have been acquired.

* * * * *